United States Patent [19]

Mische et al.

[11] Patent Number: 5,490,859
[45] Date of Patent: Feb. 13, 1996

[54] EXPANDABLE INTRAVASCULAR OCCLUSION MATERIAL REMOVAL DEVICES AND METHODS OF USE

[75] Inventors: Hans A. Mische; Thomas V. Ressemann, both of St. Cloud; Anthony C. Vrba; Steven S. Hackett, both of Maple Grove, all of Minn.

[73] Assignee: SciMed Life Systems, Inc., Maple Grove, Minn.

[21] Appl. No.: 55,995

[22] Filed: Apr. 29, 1993

Related U.S. Application Data

[63] Continuation-in-part of Ser. No. 976,199, Nov. 13, 1992.
[51] Int. Cl.$^6$ .................................................. A61B 17/22
[52] U.S. Cl. ......................... 606/159; 606/170; 606/180
[58] Field of Search ..................................... 606/159, 170, 606/171, 180, 191–200; 604/22, 96, 104, 105

[56] References Cited

U.S. PATENT DOCUMENTS

| | | |
|---|---|---|
| 1,612,697 | 12/1926 | Cecil . |
| 2,498,692 | 2/1950 | Mains . |
| 2,621,651 | 12/1952 | Wallace . |
| 2,816,552 | 12/1957 | Hoffman . |

(List continued on next page.)

FOREIGN PATENT DOCUMENTS

| | | |
|---|---|---|
| 0117519A1 | 2/1984 | European Pat. Off. . |
| 0254414A1 | 6/1987 | European Pat. Off. . |
| 0533321A2 | 3/1993 | European Pat. Off. . |
| 867144 | 12/1952 | Germany . |
| 2020557 | 11/1979 | United Kingdom . |
| WO83/03752 | 11/1983 | WIPO . |
| WO91/17714 | 11/1991 | WIPO . |
| WO92/03098 | 3/1992 | WIPO . |
| WO92/03097 | 3/1992 | WIPO . |
| WO93/01849 | 2/1993 | WIPO . |
| WO94/10919 | 5/1994 | WIPO . |

OTHER PUBLICATIONS

Technical Bulletin P.B.S. vs. Electroplating Abrasive Technology, Inc. from Manufacturers of Diamond and CBN Products for Industry.
Percutaneous Aspiration Thromboembolectomy, Interventional Radiology, Jul. 1985, 156:61–66.

(List continued on next page.)

*Primary Examiner*—Stephen C. Pellegrino
*Assistant Examiner*—William W. Lewis
*Attorney, Agent, or Firm*—Nawrocki, Rooney & Sivertson

[57] ABSTRACT

An intravascular occlusion material removal device for removing vascular occlusion material in a vascular lumen comprises an expandable material removal element movable between an expanded position and a contracted position. The material removal element has a distal end and a proximal end. A drive shaft is operatively connected to the distal end of the expandable material removal element for rotating the removal element. A catheter surrounds a portion of the drive shaft. The catheter has a distal end for operatively variably contacting the proximal end of the material removal element such that the removal element is rotatable with respect to the catheter. The catheter is shiftable with respect to the drive shaft for moving the material removal element between the expanded position and the contracted position. A number of novel methods for removing vascular occlusion material are also provided. One such method comprises the steps of: providing a vascular occlusion material removal device having an expandable occlusion material removal element, wherein the removal element comprises a plurality of braided wires, further comprising an abrasive disposed on the wires; providing a drive shaft disposed in and shiftable with respect to the removal element; intravascularly positioning the removal element distally of the occlusion material; shifting the drive shaft with respect to the removal element to expand the element intravascularly; and moving the removal element proximally within the vascular lumen to remove occlusion material. The removal element can also be moved distally within the vascular lumen to engage the occlusion material. Also, removed occlusion material can be collected by a collection portion on the removal element.

63 Claims, 10 Drawing Sheets

U.S. PATENT DOCUMENTS

| | | |
|---|---|---|
| 3,320,957 | 5/1967 | Sokolik . |
| 3,352,303 | 11/1967 | Delaney . |
| 3,416,531 | 12/1968 | Edwards . |
| 3,433,226 | 3/1969 | Boyd . |
| 3,485,234 | 12/1969 | Stevens . |
| 3,568,659 | 3/1971 | Karnegis . |
| 3,605,725 | 9/1971 | Bentov . |
| 3,623,483 | 11/1971 | Dyer, Jr. . |
| 3,692,029 | 9/1972 | Adair . |
| 3,773,034 | 11/1973 | Burns et al. . |
| 3,788,318 | 1/1974 | Kim et al. . |
| 3,789,952 | 2/1974 | Kim et al. ............................. 128/347 |
| 3,868,956 | 3/1975 | Alfidi et al. . |
| 3,894,673 | 7/1975 | Lowder et al. . |
| 3,923,065 | 12/1975 | Nozick et al. . |
| 3,965,909 | 6/1976 | Waddell et al. . |
| 3,968,800 | 7/1976 | Vilasi . |
| 3,996,938 | 12/1976 | Clark, III . |
| 4,018,576 | 4/1977 | Lowder et al. . |
| 4,046,150 | 9/1977 | Schwartz et al. . |
| 4,137,906 | 2/1979 | Akiyama et al. . |
| 4,177,815 | 12/1979 | Patel . |
| 4,195,637 | 4/1980 | Grüntzig et al. . |
| 4,307,722 | 12/1981 | Evans . |
| 4,323,071 | 4/1982 | Simpson et al. . |
| 4,347,846 | 9/1982 | Dormia . |
| 4,445,509 | 5/1984 | Auth . |
| 4,465,072 | 8/1984 | Taheri . |
| 4,572,186 | 2/1986 | Gould et al. . |
| 4,577,631 | 3/1986 | Kreamer . |
| 4,607,618 | 8/1986 | Angelchik . |
| 4,679,557 | 7/1987 | Opie et al. . |
| 4,696,667 | 9/1987 | Masch . |
| 4,732,154 | 3/1988 | Shiber . |
| 4,784,636 | 11/1988 | Rydell ..................................... 606/159 |
| 4,819,634 | 4/1989 | Shiber . |
| 4,838,853 | 6/1989 | Parisi . |
| 4,842,579 | 6/1989 | Shiber . |
| 4,883,458 | 11/1989 | Shiber . |
| 4,885,003 | 12/1989 | Hillstead .................................. 604/22 |
| 4,886,061 | 12/1989 | Fischell et al. . |
| 4,886,490 | 12/1989 | Shiber . |
| 4,894,051 | 1/1990 | Shiber . |
| 4,895,166 | 1/1990 | Farr et al. . |
| 4,895,560 | 1/1990 | Papantonakos . |
| 4,921,484 | 5/1990 | Hillstead . |
| 4,957,482 | 9/1990 | Shiber . |
| 4,966,604 | 10/1990 | Reiss . |
| 4,979,939 | 12/1990 | Shiber . |
| 4,990,134 | 2/1991 | Auth . |
| 5,002,553 | 3/1991 | Shiber . |
| 5,007,896 | 4/1991 | Shiber . |
| 5,009,659 | 4/1991 | Hamlin et al. . |
| 5,011,488 | 4/1991 | Ginsburg . |
| 5,024,651 | 6/1991 | Shiber . |
| 5,030,201 | 7/1991 | Palestrant . |
| 5,041,082 | 8/1991 | Shiber . |
| 5,100,425 | 3/1992 | Fischell et al. . |
| 5,116,350 | 5/1992 | Stevens . |
| 5,135,531 | 8/1992 | Shiber . |
| 5,154,724 | 10/1992 | Andrews . |
| 5,165,421 | 11/1992 | Fleischhacker et al. . |
| 5,176,693 | 1/1993 | Pannek, Jr. . |
| 5,314,407 | 5/1994 | Auth et al. . |
| 5,314,438 | 5/1994 | Shturman . |

OTHER PUBLICATIONS

Mechanical Spiral Embolectomy Catheter, Irvin F. Hawkins, Jr., M.D., et al., Seminars in Interventional Radiology, vol. 2, No. 4, Dec. 1985, pp. 414–418.

PAT–RAT Acc. to "Starck"–Rotational Aspiration Thromboembolectomy, Angiomed.

Percutaneous Embolectomy by Transcatheter Aspiration, Kenneth W. Sniderman, M.D., et al., Radiology, Feb. 1984 150:357–361.

Percutaneous Transluminal Thrombus Aspiration, E. Starck et al., Angiographic Management of Vascular Obstruction, pp. 625–632.

Advantages of Percutaneous Aspiration Thromboembolectomy, E. Starck et al., pp. 241–247.

Mechanical Thrombectomy, S. Murthy Tadavarthy, M.D., Interventional Radiology, vol. 1, Second Edition, pp. 635–664.

Transvenous Removal of Pulmonary Emboli by Vacuum–Cup Catheter Technique, Lazar J. Greeenfield, M.D., Journal of Surgical Research, vol. 9, No. 6, Jun. 1969, pp. 347–352.

Balloon Embolectomy Catheter Used Percutaneously, John C. McDermott, M.D., Radiology, vol. 160, No. 1, p. 279.

Correspondence and Brief Communications/Calendar of Events, Arch Surg—vol. 120, Jan. 1985, p. 116.

Percutaneous Aspiration Thromboembolectomy (PAT): An Alternative to Surgical Balloon Techniques for Clot Retrieval, William D. Turnipseed, M.D., et al., Journal of Vascular Surgery, vol. 3, No. 3, Mar. 1986, pp. 437–441.

Peripheral Percutaneous Aspiration Thrombectomy and Angioplasty Following Failed Lytic Therapy for Acute Popliteal Artery Occulusion, George Li, M.D., Journal of Interventional Cardology, vol. 5, No. 3, 1992, pp. 159–162.

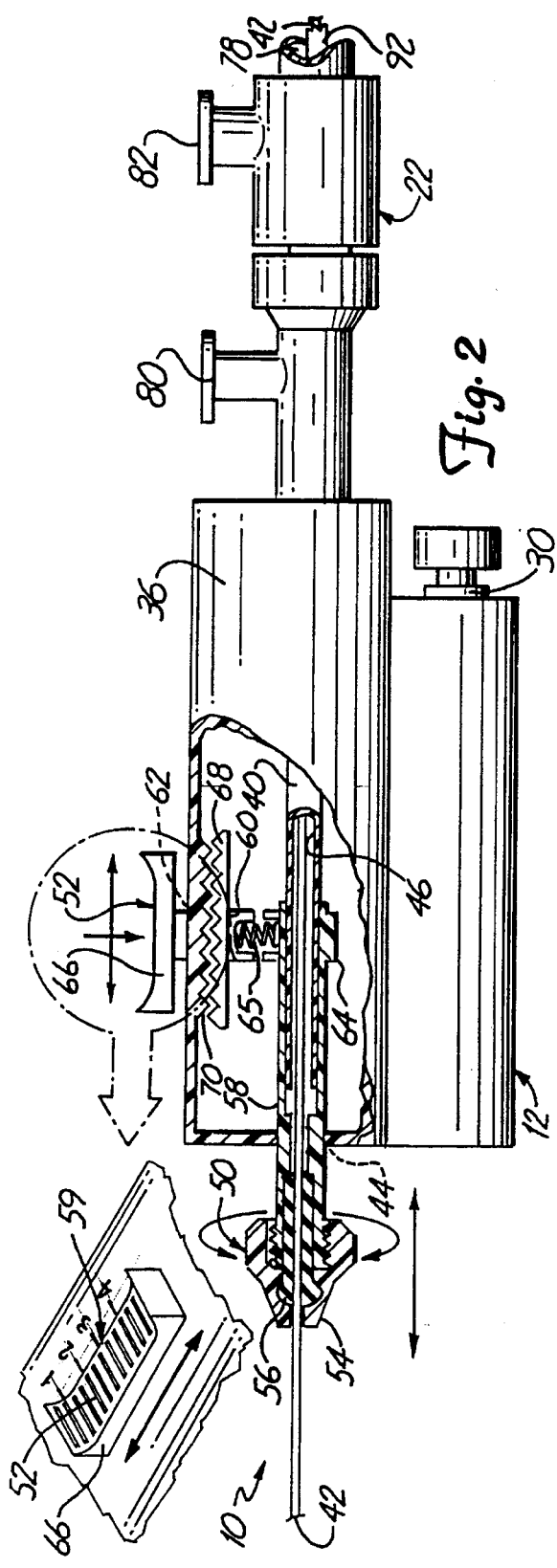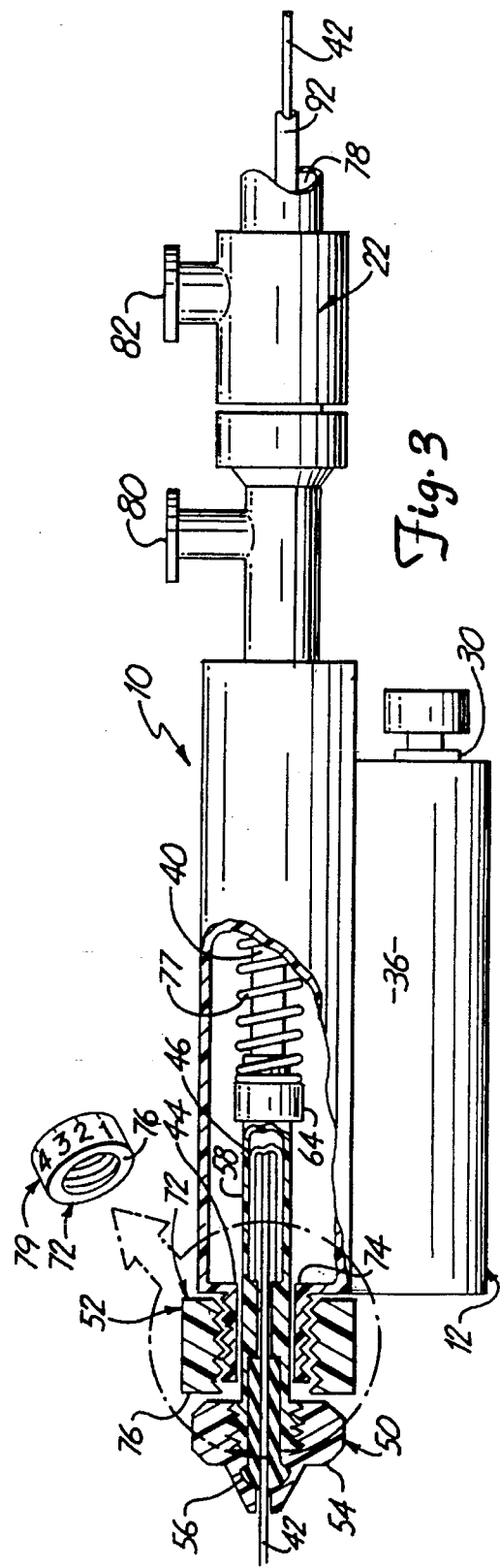

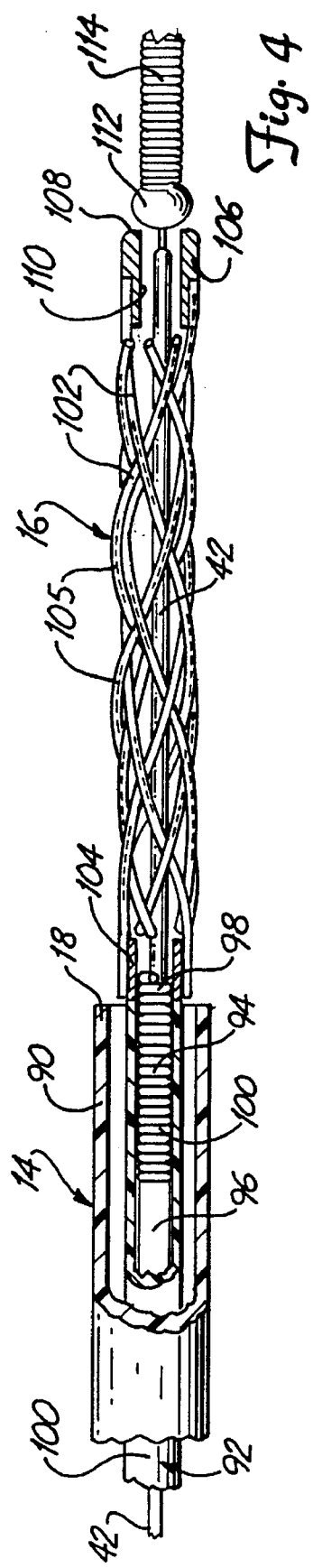
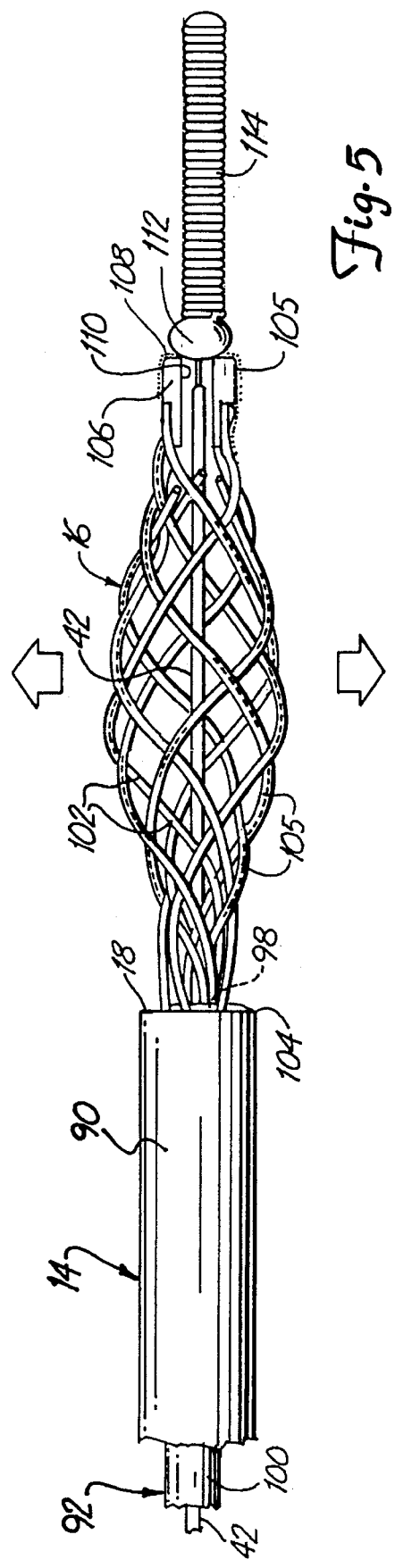
Fig. 4
Fig. 5

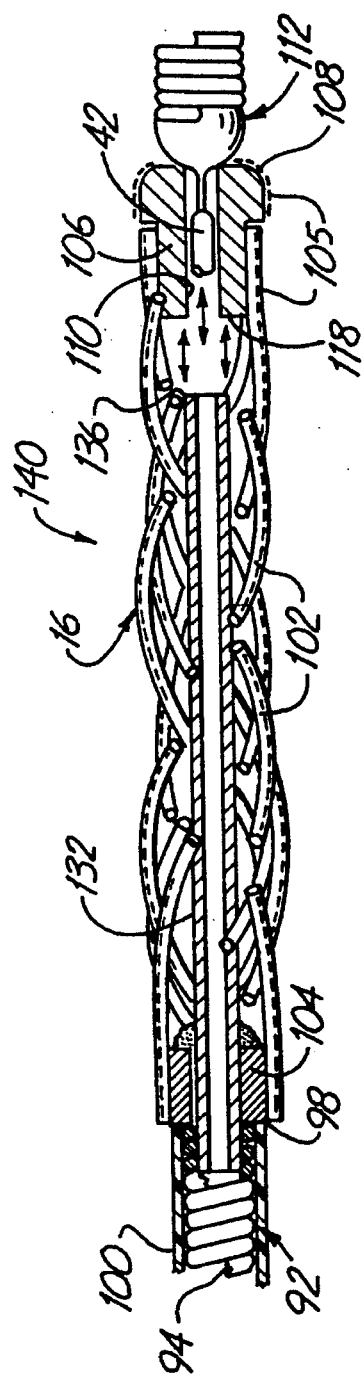
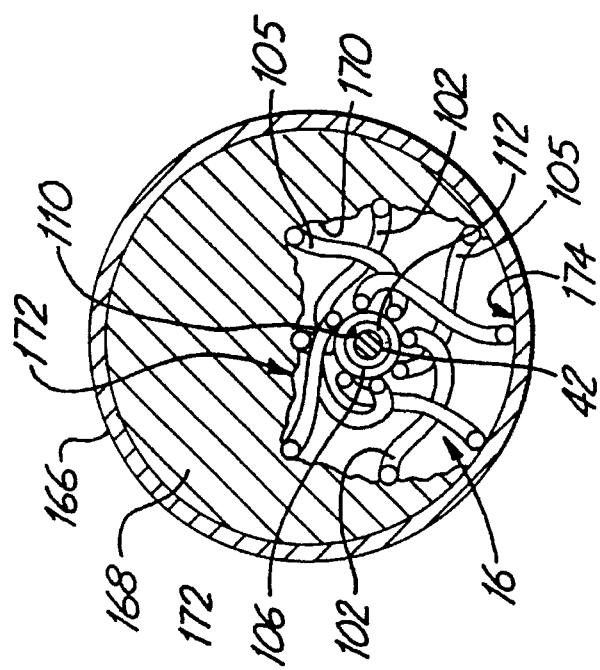

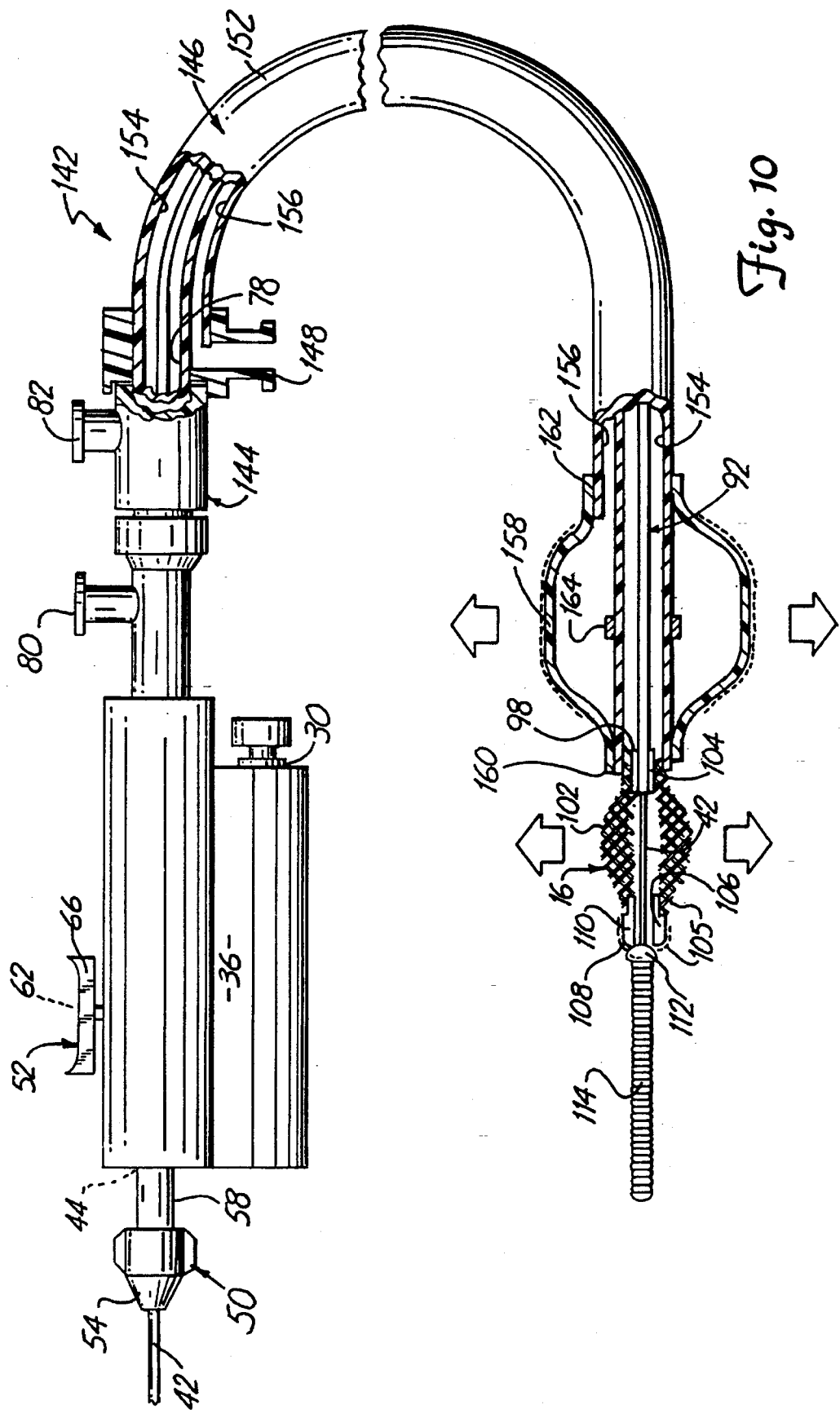

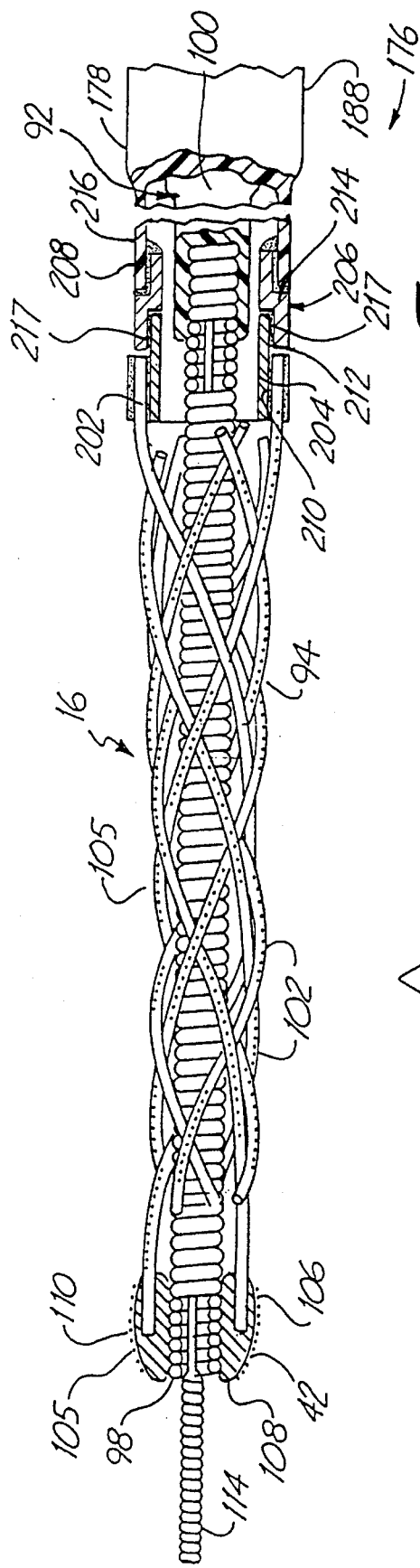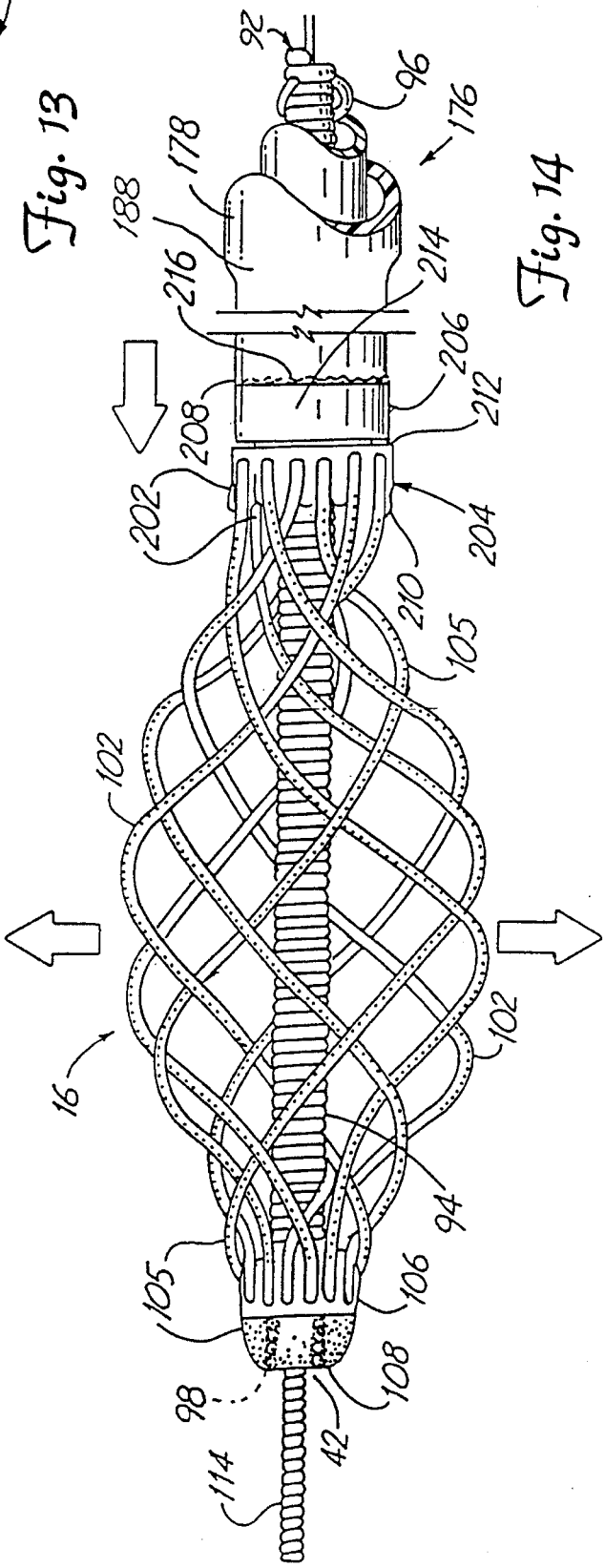

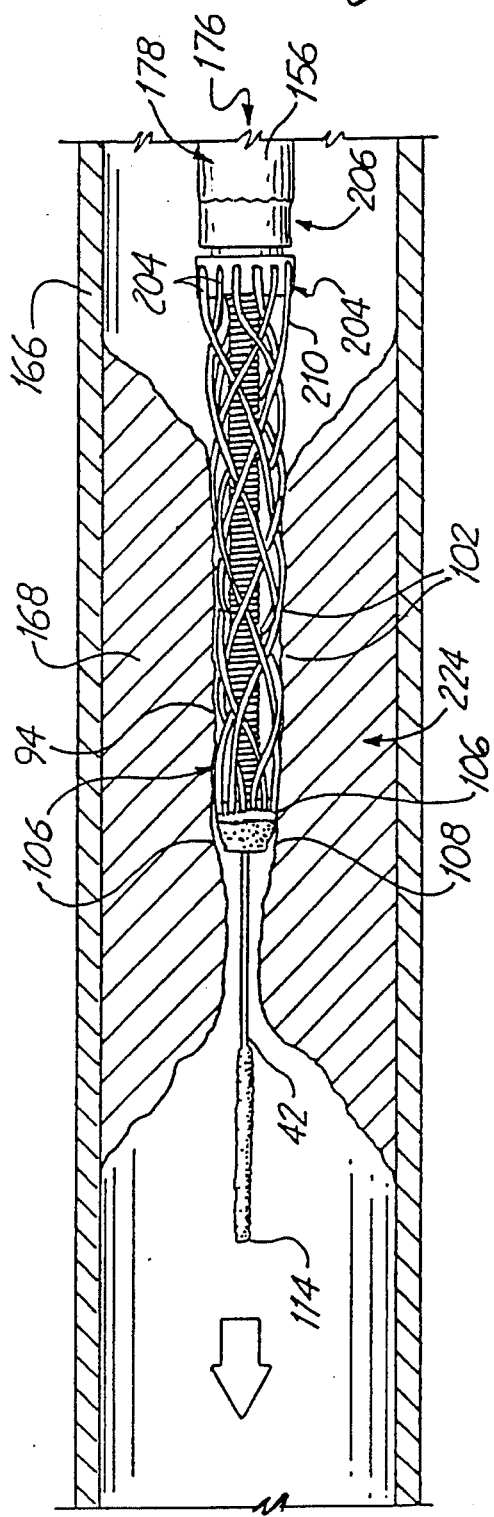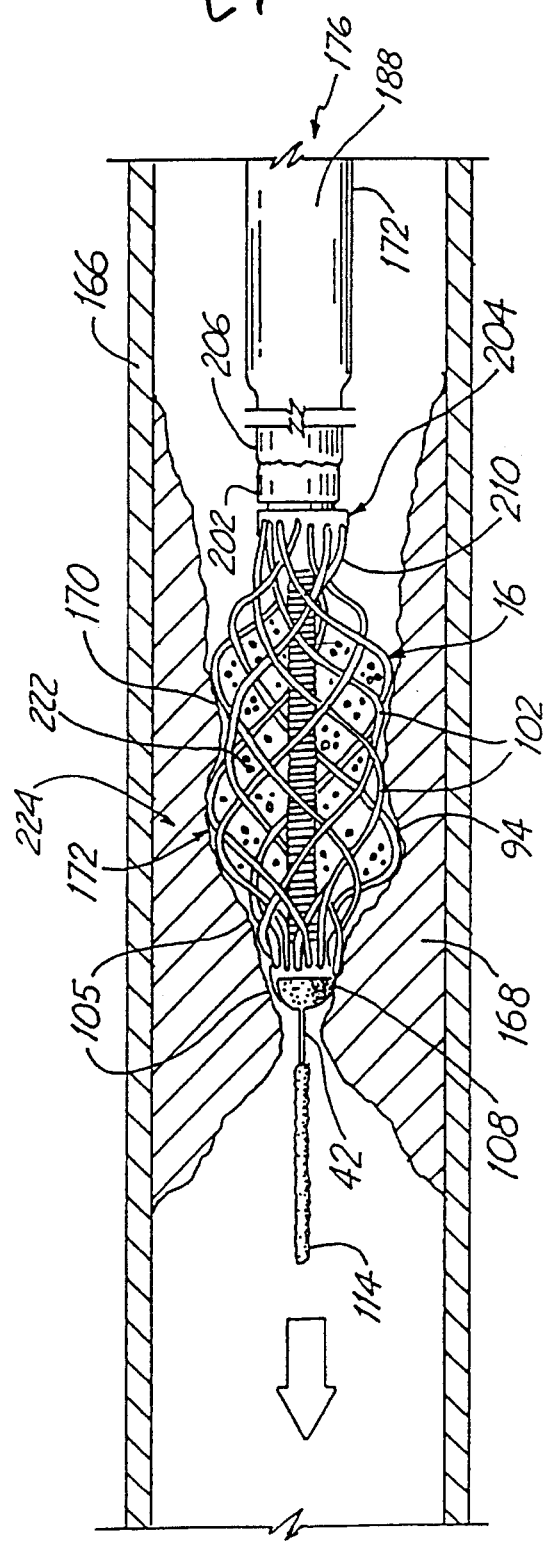

EXPANDABLE INTRAVASCULAR OCCLUSION MATERIAL REMOVAL DEVICES AND METHODS OF USE

REFERENCES TO RELATED APPLICATIONS

This application is a continuation-in-part of the U.S. patent application of Mische et al., Ser. No. 07/976,199, filed on Nov. 13, 1992.

BACKGROUND OF THE INVENTION

The present invention generally relates to constructions for intravascular treatment devices useful for removing vascular occlusion material from a vascular occlusion or from a vascular lumen. The invention more specifically relates to expandable intravascular occlusion material removal devices, as well as to methods of using those devices to treat vascular diseases.

Vascular diseases, such as atherosclerosis and the like, have become quite prevalent in the modern day. These diseases may present themselves in a number of forms. Each form of vascular disease may require a different method of treatment to reduce or cure the harmful effects of the disease. Vascular diseases, for example, may take the form of deposits or growths in a patient's vasculature which may restrict, in the case of a partial occlusion, or stop, in the case of a total occlusion, blood flow to a certain portion of the patient's body. This can be particularly serious if, for example, such an occlusion occurs in a portion of the vasculature that supplies vital organs with blood or other necessary fluids.

To treat these diseases, a number of different therapies are being developed. While a number of invasive therapies are available, it is desirable to develop non-invasive therapies as well. Non-invasive therapies may be less risky than invasive ones, and may be more welcomed by the patient because of the possibility of decreased chances of infection, reduced post-operative pain, and less post-operative rehabilitation. One type of non-invasive therapy for vascular diseases is pharmaceutical in nature. Clot-busting drugs have been employed to help break up blood clots which may be blocking a particular vascular lumen. Other drug therapies are also available. Further non-invasive, intravascular treatments exist that are not only pharmaceutical, but also revascularize blood vessels or lumens by mechanical means. Two examples of such intravascular therapies are balloon angioplasty and atherectomy which physically revascularize a portion of a patient's vasculature.

Balloon angioplasty comprises a procedure wherein a balloon catheter is inserted intravascularly into a patient through a relatively small puncture, which may be located proximate the groin, and intravascularly navigated by a treating physician to the occluded vascular site. The balloon catheter includes a balloon or dilating member which is placed adjacent the vascular occlusion and then is inflated. Intravascular inflation of the dilating member by sufficient pressures, on the order of 5 to 12 atmospheres or so, causes the balloon to displace the occluding matter to revascularize the occluded lumen and thereby restore substantially normal blood flow through the revascularized portion of the vasculature. It is to be noted, however, that this procedure does not remove the occluding matter from the patient's vasculature, but displaces it.

While balloon angioplasty is quite successful in substantially revascularizing many vascular lumens by reforming the occluding material, other occlusions may be difficult to treat with angioplasty. Specifically, some intravascular occlusions may be composed of an irregular, loose or heavily calcified material which may extend relatively far along a vessel or may extend adjacent a side branching vessel, and thus are not prone or susceptible to angioplastic treatment. Even if angioplasty is successful, thereby revascularizing the vessel and substantially restoring normal blood flow therethrough, there is a chance that the occlusion may recur. Recurrence of an occlusion may require repeated or alternative treatments given at the same intravascular site.

Accordingly, attempts have been made to develop other alternative mechanical methods of non-invasive, intravascular treatment in an effort to provide another way of revascularizing an occluded vessel and of restoring blood flow through the relevant vasculature. These alternative treatments may have particular utility with certain vascular occlusions, or may provide added benefits to a patient when combined with balloon angioplasty and/or drug therapies.

One such alternative mechanical treatment method involves removal, not displacement, as is the case with balloon angioplasty, of the material occluding a vascular lumen. Such treatment devices, sometimes referred to as atherectomy devices, use a variety of means, such as lasers, and rotating cutters or ablaters, for example, to remove the occluding material. The rotating cutters may be particularly useful in removing certain vascular occlusions. Since vascular occlusions may have different compositions and morphology or shape, a given removal or cutting element may not be suitable for removal of a certain occlusion. Alternatively, if a patient has multiple occlusions in his vasculature, a given removal element may be suitable for removing only one of the occlusions. Suitability of a particular cutting element may be determined by, for example, its size or shape. Thus, a treating physician may have to use a plurality of different treatment devices to provide the patient with complete treatment. This type of procedure can be quite expensive because multiple pieces of equipment may need to be used (such intravascular devices are not reusable because they are inserted directly into the blood stream), and may be tedious to perform because multiple pieces of equipment must be navigated through an often-tortuous vascular path to the treatment site.

SUMMARY OF THE INVENTION

A general object of an embodiment of the present invention is to provide improved constructions for vascular occlusion material removal elements and associated intravascular devices.

A more specific object of an embodiment of the invention is to provide an expandable intravascular device for removing vascular occlusion material from a vascular surface.

Another object of an embodiment of the present invention is to provide an expandable intravascular device which has a profile smaller than the profiles of some expandable intravascular devices.

An additional object of an embodiment of the invention is to provide an expandable intravascular device which has a construction simpler than the constructions of some expandable intravascular devices.

An intravascular device, constructed according to the teachings of the present invention, for removing vascular occlusion material in a vascular lumen comprises an expandable material removal element movable between an expanded position and a contracted position. The material removal element has a distal end and a proximal end. A drive shaft is operatively connected to the distal end of the expandable material removal element for rotating the removal element. A catheter surrounds a portion of the drive shaft. The catheter has a distal end for operatively variably contacting the proximal end of the material removal element such that the removal element is rotatable with respect to the catheter. The catheter is shiftable with respect to the drive shaft for moving the material removal element between the expanded position and the contracted position. One such method comprises the steps of: providing a vascular occlusion material removal device having an expandable occlusion material removal element, wherein the removal element comprises a plurality of braided wires, further comprising an abrasive disposed on the wires; providing a drive shaft disposed in and shiftable with respect to the removal element; intravascularly positioning the removal element distally of the occlusion material; shifting the drive shaft with respect to the removal element to expand the element intravascularly; and moving the removal element proximally within the vascular lumen to remove occlusion material. The removal element can also be moved distally within the vascular lumen to engage the occlusion material. Also, removed occlusion material can be collected by a collection portion on the removal element.

A number of methods, according to the teachings of the present invention, for removing vascular occlusion material are provided. One such method comprises the steps of: providing a vascular occlusion material removal device having an expandable occlusion material removal element, wherein the removal element comprises a plurality of braided wires, further comprising an abrasive disposed on the wires; providing a drive shaft disposed in and shiftable with respect to the removal element; intravascularly positioning the removal element distally of the occlusion material; shifting the drive shaft with respect to the removal element to expand the element intravascularly; and moving the removal element proximally within the vascular lumen to remove occlusion material. The removal element can also be moved distally within the vascular lumen to engage the occlusion material. Also, removed occlusion material can be collected by a collection portion on the removal element.

BRIEF DESCRIPTION OF THE DRAWINGS

The organization and manner of the structure and operation of the invention, together with further advantages thereof, may best be understood by reference to the following description taken in connection with the accompanying drawings, wherein like reference numerals identify like elements in which:

FIG. 2 is an enlarged partially sectioned side elevational view of a proximal portion of the occlusion material removal device of FIG. 1;

FIG. 3 is a view, similar to that of FIG. 2, of an alternative embodiment of the proximal portion of the occlusion material removal device of FIG. 1;

FIG. 4 is an enlarged, partially sectioned side elevational view of a distal portion of the occlusion material removal device of FIG. 1 showing an expandable material removal element in a contracted position;

FIG. 5 is a view, similar to that of FIG. 4 illustrating the expandable material removal element in an expanded position;

FIG. 9 is a view, similar to that of FIG. 8, of yet a further embodiment of the distal portion;

FIG. 10 is a view, similar to that of FIG. 1, of another embodiment of the expandable occlusion material removal device having a dilating member at a distal portion thereof;

FIG. 11 is a sectional view of an expandable occlusion material removal element disposed within an occluded vascular lumen showing the conformity of the removal element to the non-occluded lumen;

FIG. 13 is an enlarged sectional view of a distal end of the removal device of FIG. 12 showing the removal element in a contracted position;

FIG. 14 is a view, similar to that of FIG. 13, illustrating the removal element in an expanded position;

FIG. 15 is a sectional view of the removal element of FIG. 14 in a contracted position forming a pilot hole through an occlusion within a vascular lumen;

FIG. 16 is a view, similar to that of FIG. 15, showing the removal element expanded against the occlusion.

DETAILED DESCRIPTION OF PREFERRED EMBODIMENTS

Figure 1:
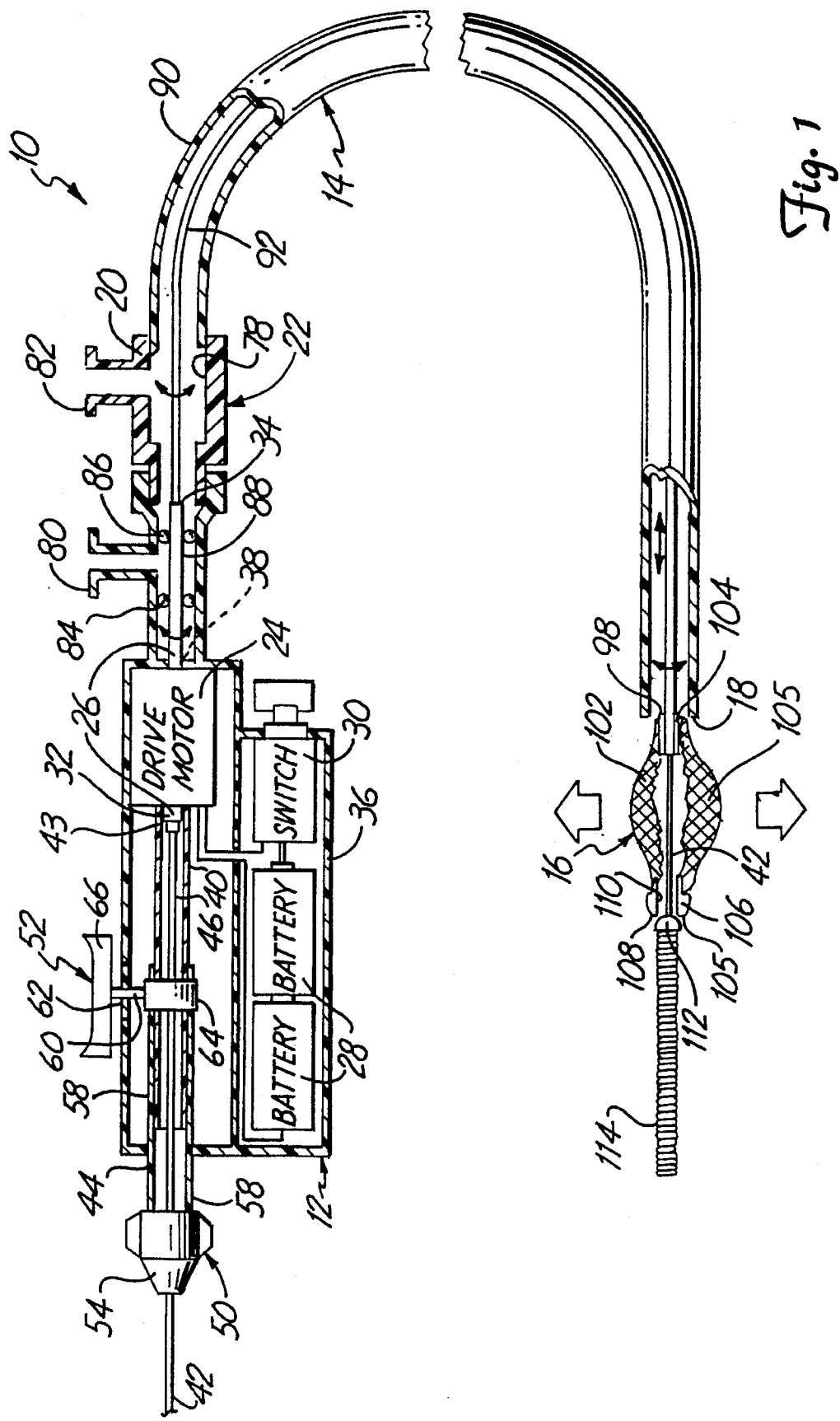
FIG. 1 is a partially sectioned side elevational view of an expandable vascular occlusion material removal device.

While the invention may be susceptible to embodiment in different forms, there are shown in the drawings, and herein will be described in detail, specific embodiments with the understanding that the present disclosure is to be considered an exemplification of the principles of the invention, and is not intended to limit the invention to that as illustrated and described herein.

The various embodiments of the present invention provide a number of constructions of expandable vascular occlusion material removal devices, intravascular material removal elements, and the like, which can be utilized to perform a plurality of different intravascular treatments, such as atherectomy, thrombectomy, angioplasty and the like. The embodiments of the present invention also provide a plurality of methods for using those devices and their associated vascular occlusion material removal elements for performing intravascular treatments on a patient. It is to be fully recognized that the different teachings of the below-discussed embodiments can be employed separately or in any suitable combination to produce desired results. The embodiments provide, in the form of expandable intravascular removal elements, ways of changing cutting or removing profiles, configurations or characteristics of a particular intravascular treatment device while only using a single removal element.

Referring initially to FIG. 1, an expandable intravascular occlusion material removal device 10 is illustrated. The removal device 10 generally comprises a drive assembly 12, a catheter assembly 14, and an expandable material removal element 16 located at a distal end 18 of the catheter assembly 14. A proximal end 20 of the catheter assembly 14 is connected to a manifold assembly 22 which forms a connection between the drive assembly 12 and the catheter assembly 14.

The constructions of the drive assembly 12 and the manifold assembly 22 are more clearly shown in FIGS. 1 and 2. The drive assembly 12 generally comprises an electric motor 24 having a hollow, rotatable drive shaft 26, a power source 28, illustrated as a plurality of batteries electrically connected in series, for energizing the motor 24, and a control switch 30 connected electrically between the motor 24 and the power source 28 such that actuation of the control switch 30 allows current to flow between the power source 28 and the motor 24, thereby causing the drive shaft 26 to rotate. In an exemplary embodiment of the invention, the motor 24 is a direct current micro-motor available from Micro Mo Electronics, Inc. of St. Petersburg, Fla., series number 2233-04.5S, and the power source 28 is a pair of 3 Volt lithium batteries. The motor 24 can rotate the drive shaft 26 at a speed of about 10,000 revolutions per minute, but it is envisioned that greater speeds, on the order of 100,000 revolutions per minute may be possible with different motors 24. For example, the motor 24 may be similar to the brushless direct current motor available from Transicoil Inc. of Valley Forge, Pa., model number U-222285, which can reach speeds of 100,000 revolutions per minute. By rotating the drive shaft 26 at this speed, more efficient removal of occlusion material may be achieved because the intravascular treatment may take less time. Thus, the removal device 10 can operate at speeds substantially within the range of 0 to 100,000 revolutions per minute. As FIG. 1 shows, the drive shaft 26 extends through the motor 24 with a proximal end 32 thereof projecting from a proximal end of the motor 24, and with a distal end 34 thereof extending out of an aperture 38 located on a distal end of a housing 36 which contains elements of the drive assembly 12. The significance of this structure will become clear later.

An inner hollow tube or sheath 40 is located between an inner, proximal end of the housing 36 and the proximal end of the motor 24 such that the proximal end 32 of the drive shaft 26 extends into the hollow interior of the inner sheath 40. The inner sheath 40 defines a lumen 46 of dimensions sufficient for accepting a medical guidewire 42, made of stainless steel, nitinol, and the like, which can extend from the guidewire lumen 46 within the inner sheath 40, and through an aperture 44 in the proximal end of the housing 36 to the exterior of the housing 36. Because the drive shaft 26 of the motor 24 is hollow, the guidewire 42 can pass through the catheter assembly 14, into the manifold assembly 22 and into the drive shaft 26. A fluid seal 43, such as a diaphragm and the like, is provided at the proximal end 32 of the drive shaft 26 so that fluid within the drive shaft 26 cannot leak into the interior of the housing 36. However, the fluid seal 43 is of appropriate construction to allow the guidewire 42 to extend from the drive shaft 26 into the inner sheath 40.

The distal end 34 of the drive shaft 26 of the motor 24 is fixedly connected to a hollow drive shaft 92 which extends axially through the catheter assembly 14 and is connected to the material removal element 16. In an exemplary embodiment, the drive shaft 92 has an outer diameter of about 0.025". The hollow drive shaft 92 also defines a guidewire lumen, thereby allowing for passage of the guidewire 42 from the material removal element 16 to the exterior of the housing 36. Thus, the removal device 10 is of an over-the-wire construction which can facilitate removing the device 10 from, and replacing the device 10 in the patient because the guidewire 42 can remain within the patient. Comparatively, some prior art devices require removal of the guidewire along with the device, thereby necessitating additional intravascular navigation not only of the device, but also of the guidewire to replace the device adjacent the occlusion material to be removed. In addition, the presence of the guidewire 42 facilitates intravascular navigation of the removal device 10, because the device 10 can be delivered over the guidewire 42, which is an improvement over some expandable intravascular devices.

The guidewire 42 is also axially shiftable with respect to the drive assembly 12 and the catheter assembly 14 so that shifting of the guidewire 42 induces corresponding movement of the material removal element 16 between a contracted position (FIG. 4) and an expanded position (FIG. 5). This operation will be discussed in greater detail hereinbelow. The guidewire 42 must have sufficient strength to transmit force to the material removal element 16 to cause movement between the contracted and expanded positions. This is an important distinction from some prior art devices which require a mechanism in addition to a medical guidewire to expand an element intravascularly. Thus, the expandable intravascular occlusion material removal device 10 is of a construction substantially simpler than some of the prior art devices. A variable length of the guidewire 42 can be shifted distally of the removal element 16 for facilitating intravascular navigation of the removal device 10. In an exemplary embodiment of the removal device 10, the guidewire 42 has an outer diameter measuring substantially within the range of 0.010" to 0.014". Also, the guidewire 42 may be coated with a low friction coating, such as a nickel-silver alloy like nikasil, or a fluoropolymer infused nickel substance like nedox, for reducing friction between the guidewire 42 and the removal device 10.

Because axial shifting of the guidewire 42 causes expansion or contraction of the material removal element 16, the drive assembly 12 includes structures for providing a treating physician with positive control over axial movement of the guidewire 42. Specifically, as shown in FIG. 2, the drive assembly 12 includes a guidewire lock mechanism 50 and a material removal element expansion control mechanism 52, both of which serve to positively control expansion or contraction of the material removal element 16 by controlling axial shifting of the guidewire 42. The guidewire lock mechanism 50 holds the guidewire 42 fixed with respect to itself and to the control mechanism 52 which allows a treating physician to positively axially shift the guidewire 42 and the guidewire lock mechanism 50 by actuation of the expansion control mechanism 52, as will be discussed in greater detail later.

The guidewire lock mechanism 50 is located at a proximal end of the housing 36 adjacent the aperture 44. The guidewire lock mechanism 50 may function substantially similarly to a pin vise, and comprises a wire lock knob 54 and an inner collet 56, shown in section in FIG. 2, through which the guidewire 42 passes. The wire lock knob 54 and the inner collect 56 are disposed at a proximal end of an outer hollow tube or sheath 58 which also passes through the aperture 44 into the interior of the housing 36. The outer sheath 58 accepts the guidewire 42 and also the inner sheath 40. The outer sheath 58 is axially shiftable with respect to the inner sheath 40, and slides along an outer surface of the inner sheath 40, which remains fixed within the housing 36, responsive to actuation of the expansion control mechanism 52, as will be discussed below.

A portion of the inner collet 56 extends into the interior of the outer sheath 58 where that portion can engage an outer diameter surface of the guidewire 42. The wire lock knob 54 is rotatable with respect to the inner collet 56 and the outer sheath 58, and is threaded vailably onto the proximal end of the outer sheath 58. Thus, as the wire lock knob 54 is appropriately rotated with respect to the inner collet 56 and the outer sheath 58, the wire lock knob 54 moves distally along the outer sheath 58 by means of the threaded engagement therebetween, which forces the inner collet 56 to engage the outer surface of the guidewire 42. The wire lock knob 54 is rotated on the outer sheath 58 sufficiently to compress the inner collet 56 against the guidewire 42 such that the guidewire 42 is fixed with respect to the guidewire lock mechanism 50 and the outer sheath 58. However, the outer sheath 58 is axially shiftable with respect to the inner sheath 40, the motor 24 and the drive shaft 26 responsive to actuation of the expansion control mechanism 52. Thus, the guidewire 42 is also positively shiftable responsive to movement of the control mechanism 52. Proper application of the guidewire lock mechanism 50 to the guidewire 42 allows a physician to positively vary expansion and/or contraction of the expandable material removal element 16. To release the guidewire 42 from the grip of the inner collet 56 and the wire lock mechanism 50, the wire lock knob 54 is rotated in an opposite direction, thereby allowing a portion of the inner collet 56 to move out of the outer sheath 58, and out of engagement with the outer surface of the guidewire 42.

The material removal element expansion control mechanism 52 is operatively connected to the outer sheath 58 such that actuation of the control mechanism 52 causes conjoint motion of the outer sheath 58 and the guidewire 42, which causes expansion and/or contraction of the material removal element 16 (assuming that the wire lock mechanism 50 holds the guidewire 42 fixed with respect to the control mechanism 52 and the outer sheath 58). Specifically, the material removal element expansion control mechanism 52 comprises a shaft 60 extending substantially perpendicularly from the inner sheath 40 and the outer sheath 58 through an elongate slot 62 in the housing 36. One end of the shaft 60 is connected to a shoulder portion 64 located adjacent a distal end of the outer sheath 58 by a compressible spring 65. The spring 65 biases the shaft 60 away from the outer sheath 58. An opposite end of the shaft 60 extends out of the housing 36 through the slot 62 where it is connected to a thumb pad 66. The thumb pad 66 is configured for facilitating application of a force from a treating physician's thumb to induce axial shifting of the guidewire 42, and thus, corresponding expansion and/or contraction of the expandable material removal element 16.

Means is provided within the housing 36 to facilitate positive shifting of the guidewire 42, and also positive movement of the expandable material removal element 16 between the expanded and contracted positions. Specifically, in the illustrated embodiment, a first set of teeth 68 is attached to the shaft 60 such that the teeth 68 extend perpendicularly with respect to an axis of elongation of the shaft 60 and substantially parallel with respect to an adjacent portion of the housing 36. Because the shaft 60 can move against the spring 65 under the influence of forces applied to the thumb pad 66, the first set of teeth 68 is also movable in corresponding fashion. A second set of teeth 70 depend from the interior surface of the housing 36 adjacent the slot 62 such that the first set of teeth 68 is interengagable with the second set of teeth 70. The second set of teeth 70 is fixed with respect to the housing 36 such that, when the teeth 68 and 70 are interengaged, the outer sheath 58 is fixed with respect to the housing 36. This prevents axial shifting of the guidewire 42 with respect to the drive assembly 12, the catheter assembly 14, and the removal element 16 if the guidewire lock mechanism 50 is applied.

The structure of the guidewire lock mechanism 50 and the material removal element expansion control mechanism 52 may be more readily understood with reference to the following discussion of the operation thereof. The guidewire 42 is disposed through the drive shaft 26, the motor 24, the inner sheath 40, the outer sheath 58, the inner collet 56 and the wire lock knob 54. The wire lock knob 54 is rotated with respect to the outer sheath 58 such that threads on the lock knob 54 and the outer sheath 58 cooperate to cause distally directed movement of the lock knob 54 with respect to the outer sheath 58. Distally directed movement of the lock knob 54 forces the inner collet 56 progressively further into the interior of the outer sheath 58. As the inner collet 56 moves into the outer sheath 58, a portion of the inner collet 56 within the outer sheath 58 engages an outer surface of the guidewire 42. The wire lock knob 54 is rotated on the outer sheath 58 so that the portion of the inner collet 56 engages the outer surface of the guidewire 42 with sufficient force to hold the guidewire 42 fixed with respect to the outer sheath 58 and the guidewire lock mechanism 50. The guidewire 42, the guidewire lock mechanism 50 and the outer sheath 58 now move conjointly.

A treating physician applies an appropriate force to the thumb pad 66, thereby causing movement of the shaft 60 towards the shoulder portion 64 of the outer sheath 58 and compressing the spring 65 between an end of the shaft 60 and the shoulder portion 64 of the outer sheath 58. Sufficient movement of the shaft 60 towards the shoulder portion 64 and sufficient compression of the spring 65 disengages the teeth 68 from the teeth 70 because the teeth 68 move conjointly with the shaft 60 while the teeth 70 remain fixed. The treating physician can now apply forces to the thumb pad 66 to conjointly axially shift the guidewire 42, the outer sheath 58, the guidewire lock mechanism 50 and the material removal element expansion control mechanism 52.

Specifically, the treating physician can apply forces to the thumb pad 66 to move or shift the guidewire 42 and the outer sheath 58 proximally rearwardly. This movement, as will be discussed in greater detail later, causes expansion of the material removal element 16. As these forces are applied to the thumb pad 66, those forces are transmitted to the shoulder portion 64 of the outer sheath 58. The outer sheath 58 slides proximally along the outer surface of the inner sheath 40 towards the aperture 44 in the housing 36. The range of sliding motion of the outer sheath 58 along the inner sheath 40 is limited by engagement of a proximal end of the teeth 68 with the adjacent interior surface of the housing 36, as well as by the dimensions of the elongate slot 62 in which a portion of the shaft 60 moves conjointly with the outer sheath 58.

The degree of material removal element 16 expansion is directly proportional to the length of axial shifting of the guidewire 42 and the outer sheath 58 proximally. Thus, the degree of material removal element 16 expansion and/or contraction can be measured by suitable scaling means 59 or 79 disposed on the housing 36 adjacent the elongate slot 62. When a desired degree of material removal element 16 expansion has been achieved, the thumb pad 66 can be released. The spring 65 now expands and forces the teeth 68 into engagement with the teeth 70. Interengagement of the teeth 68 and 70 positively locks the axial position of the guidewire 42, and thus, also the expanded position of the material removal element 16. Because a plurality of teeth 68 and 70 are provided, the material removal element expansion control mechanism 52 allows for positively controlled, incremental expansion of the material removal element 16. To contract the expandable material removal element 16, the above-discussed steps are repeated, but this time, the treating physician moves the thumb pad 66 and the guidewire 42 distally.

An alternative embodiment of the material removal element expansion control mechanism 52 is illustrated in FIG. 3. It is to be noted that the construction of this embodiment is substantially similar to that illustrated in FIGS. 1 and 2, except for the differences noted hereinbelow, hence the like reference numerals for similar structures. The guidewire lock mechanism 50 of the embodiment of FIG. 2 is the same as that of the embodiment of FIG. 3.

Specifically, in the embodiment of FIG. 3, the material removal element expansion control mechanism 52 comprises an expansion knob 72 and a threaded hub 74. The threaded hub 74 extends from and is fixed to a proximal end of the housing 36 and surrounds the aperture 44 in the housing 36 and the outer sheath 58. The expansion knob 72 has internal threads matable with the threads on the threaded hub 74, and is disposed on the hub 74 such that the knob 72 surrounds the hub 74. The expansion knob 72 is rotatable on the threaded hub 74, and the threads thereon cooperate so that rotation of the expansion knob 72 on the threaded hub 74 causes the expansion knob 72 to move proximally or distally with respect to the hub 74, depending upon the direction of rotation. Distal movement of the expansion knob 72 causes contraction of the material removal element 16 and proximal movement of the expansion knob 72 causes expansion of the material removal element 16.

To expand the material removal element 16, the expansion knob 72 is rotated such that the knob 72 moves proximally on the threaded hub 74 so that a proximal end 76 of the expansion knob 72 contacts a distal end of the wire lock knob 54. Further proximal motion of the expansion knob 72 forces the wire lock knob 54 to shift proximally with respect to the drive assembly 12, thereby shifting the guidewire 42 proximally as well. The outer sheath 58 conjointly slides proximally along the outer surface of the inner sheath 40, as discussed above. Proximal movement of the expansion knob 72 on the threaded hub 74 is positively limited. thereby limiting the maximum size of the expandable material removal element 16. Specifically, upon sufficient rotation and proximal movement of the expansion knob 72, a proximal end of the shoulder portion 64 engages an interior proximal side of the housing 36.

The expandable material removal element 16 can be contracted by reversing the direction of rotation of the expansion knob 72. To facilitate return of the material removal element 16 from the expanded position to the contracted position, a coiled spring 77 may be disposed between the shoulder portion 64 and the proximal end of the motor 24, as shown in FIG. 3, or, alternatively, disposed between the shoulder portion 64 and the proximal end of the housing 36. The spring 77 relaxes as the expansion knob 72 moves distally on the threaded hub 74. Relaxation of the spring 77 moves the outer sheath 58, the wire lock knob 54 and the guidewire 42 proximally with respect to the drive assembly 12. Suitable scaling means 59 or 79 can be provided on the expansion knob 72 and/or the housing 36 for providing a treating physician with a positive indication of the degree of expansion and/or contraction of the expandable material removal element 16.

The construction of the manifold assembly 22 is illustrated in FIGS. 1 through 3. The manifold assembly 22 connects the drive assembly 12 to the catheter assembly 16.

The manifold assembly 22 generally comprises a main lumen 78 which extends from a distal end of the housing 36 to the proximal end 20 of the catheter assembly 14, and has at least two ports 80 and 82, accessible from the exterior of the manifold assembly 22, which communicate with the main lumen 78. The hollow drive shaft 26 of the motor 24 extends through the aperture 38 in the housing 36 and into the main lumen 78. The drive shaft 26 has a lumen therein of dimensions sufficient for accepting the guidewire 42 so that the guidewire 42 can also extend into the main lumen 78 within the drive shaft 26.

In the illustrated embodiment, the drive shaft 26 extends into the main lumen 78 a distance sufficient to locate the distal end 34 of the drive shaft 26 distally of the port 80. A pair of fluid seals 84 and 86 are provided within the main lumen 78 on opposite sides of the port 80. The fluid seals 84 and 86 extend from the main lumen 78 to an outer surface of the drive shaft 26 and form a fluid-tight seal around a portion of the drive shaft 26 therebetween. A longitudinal aperture 88 is located on the drive shaft 26 between the fluid seals 84 and 86 for allowing fluid to pass into the hollow interior of the drive shaft 26. This construction allows the port 80 to be dedicated to infusion of fluids into the drive shaft 26. This infused fluid can provide for increased lubrication between the outer surface of the guidewire 42 and the inner surface of the drive shaft 26, which may be beneficial during operation of the motor 24, and for allowing irrigation of an intravascular treatment site, which may be necessary to maintain a fluid balance within a vascular lumen if aspiration techniques are also used. Accordingly, the port 80 is connectable to a suitable fluid source, not shown, but well known in the art. The port 82 can be utilized for infusion of fluids, such as contrast media, saline, a drug therapy, and the like, into the patient, and for aspiration of the intravascular treatment site. The fluid seals 84 and 86 provide for this independent operation of the ports 80 and 82, and also insure that fluids introduced into the main lumen 78 will not reach the motor 24. To insure delivery of the fluids for infusion or negative pressures for aspiration, the port 82 communicates with a catheter sheath 90 connected to the distal end of the manifold assembly 22. The catheter sheath 90 is of well known construction, and can be made from polyethylene, KYNAR, a fluoropolymer and the like. In an exemplary embodiment, the catheter sheath 90 can have an axial length of about 133 cm and an outer diameter of about 0.072", thereby enabling it to be inserted into a 7 French guide catheter. The proximal end of the catheter sheath 90 defines the proximal end 20 of the catheter assembly 14.

The distal end 34 of the hollow drive shaft 26 is fixedly attached to another hollow drive shaft 92, which extends through the catheter sheath 90 of the catheter assembly 14, so that the drive shafts 24 and 92 rotate conjointly. The construction of the drive shaft 92 is illustrated in FIGS. 4 and 5. Specifically, the drive shaft 92 comprises an inner coil 94, preferably formed from a plurality of intertwined strands of a wire composed of a suitable metal, such as stainless steel or nitinol, wound in a predetermined direction such that the coil 94 expands radially upon rotation of the drive shaft 92. This maintains or increases the clearance between the outer stirface of the guidewire 42 and the inner surface of the coil 94. In order to limit radial and axial expansion of the inner coil 94, a wire braid 96 formed from a metal such as stainless steel, nitinol or the like, is applied over a portion of the outer diameter surface of the coil 94. Wires forming the inner coil 94 and the braid 96 can have a rounded or flattened configuration.

An end of the braid 96 is applied over the outer diameter surface of the coil 94 and attached by suitable means, such as solder, braze, and the like, to a proximal end of the inner coil 94. The braid 96 is then stretched axially or tensioned along the length of the inner coil 94, thereby closely confining radial expansion of the individual windings of the inner coil 94. Once stretched, an end of the braid 96 is attached to a portion of the inner coil 94 preferably offset proximally of a distal end 98 of the inner coil 94. This, in the illustrated embodiment, leaves a number of distal-most windings of the inner coil 94 uncovered by the braid 96, however, it is to be understood that the braid 96 can extend along the entire axial length of the coil 94 or may be entirely eliminated.

Tensioning the braid 96 over the outer diameter surface of the inner coil 94 limits the radial expansion of the coil 94 during operation of the motor 24. In addition, by covering the proximal portion of the inner coil 94 with the braid 96, the drive shaft 92 has an increased torque rigidity as compared to the coil 94 alone. Torque transfer to the expandable material removal element 16 is correspondingly increased, and the distal end 98 of the inner coil 94 is more responsive to proximally applied torques. Furthermore, by leaving a distal-most portion of the coil 94 uncovered by the braid 96, that portion is rather flexible and has increased trackability, thereby making it easier to torque the distal end 98 through tight curves within a patient's vasculature. To further improve trackability, as well as to reduce friction between the outer surface of the drive shaft 92 and the inner surface of the catheter sheath 90, a lubricous or low friction coating 100, comprised of a fluoropolymer and the like, is applied to the outer surface of the drive shaft 92. The coating 100 may be provided in the form of a sheath of a fluoropolymer which shrinks upon application of heat. In this manner, the coating 100 can reduce friction between the drive shaft 92 and the coating 100, provide the drive shaft 92 with increased torsional rigidity, limit radial expansion of the drive shaft 92, and form a fluid-tight lumen through the drive shaft 92. The coating 100 can also insure proper aspiration through the catheter sheath 90 by minimizing friction between the drive shaft 92 and occlusion material aspirated into the catheter sheath 90. Also, as shown in FIGS. 1, 4 and 5, the catheter sheath 90 terminates at a location offset proximally of the distal end 98 of the drive shaft 92 and a proximal end of the material removal element 16. This provides for proper irrigation and aspiration of an intravascular treatment site because the irrigation site is located distally of the aspiration site.

In some embodiments, the drive shaft 92 may not include the braid 96. In these embodiments, the inner coil 94 of the drive shaft 92 is formed by wires wound opposite to the intended direction of rotation of the drive shaft 92. In this manner, the coil 94 may radially expand upon rotation of the drive shaft 92. Another coil, formed by wires wound in the intended direction of drive shaft 92 rotation surrounds the inner coil 94. Because this outer coil is wound in the direction of drive shaft 92 rotation, the outer coil may radially contract upon rotation of the drive shaft 92. The radial expansion of the inner coil 94 is balanced by the radially contraction of the outer coil. Thus, the outer coil can perform substantially the same function as the braid 96. Some embodiments of the drive shaft 92 may axially expand or contract responsive to radial contraction or expansion, respectively, thereof during operation of the removal device 10. The drive shaft 92 may be constructed, by appropriately winding the inner and outer coils, to render axially expansion and/or contraction of the drive shaft 92 controllable. The axial expansion or contraction of the drive shaft 92 may also effect radial expansion of the removal element 16. This will be discussed further later.

The distal end 98 of the inner coil 94 is fixedly attached to the expandable material removal element 16 so that the drive shaft 92 and the material removal element 16 rotate conjointly. The material removal element 16 generally comprises a plurality, preferably 8 or 16, of braided wires 102. The wires 102 themselves preferably have a substantially round latitudinal cross section defining an outer diameter of about 0.002" to 0.006", although wires having flat, square, or triangular cross sections can also be used. In an exemplary embodiment of the removal element 16, the wires 102 comprise nitinol super-elastic wire, chromium-doped as drawn, having a diameter of about 0.003". In this embodiment, 16 nitinol wires 102 are braided at about 80 to 120 pics per inch and heat set at approximately 500 degrees Celsius for about 5 minutes. This embodiment of the removal element 16 has a length substantially within the range of about 1 cm to 3 cm, a contracted diameter substantially within the range of 1 mm to 1.125 mm, and a maximum expanded diameter of about 4 mm. In another exemplary embodiment, the wires 102 define a removal element 16 having an axial length of about 1.5 cm, and an outer diameter of about 1.25 mm in the contracted position. In the fully expanded position, this other embodiment of the removal element 16 can define an outer diameter measuring substantially within the range of 2.0 to 4.0 mm.

The outer surfaces of the wires 102 may be sharpened, etched or coated with an abrasive 105, such as a diamond grit and the like, to improve the removing or cutting characteristics of the material removal element 16. In one embodiment, a diamond grit having a grit size substantially within the range of 5 to 100 microns is electroplated onto the wires 102 in substantially uniform manner, however, the grit may be asymmetrically deposited on the wires 102 if desired. In another exemplary embodiment, the abrasive 105 may comprise a diamond grit or synthetic abrasive, such as a cubic boron nitride and the like, having a grit size approximately within the range of 10 to 25 microns, attached to the wires 102 by a nickel electroplating process. The electroplating process may be substantially similar to that disclosed in U.S. Pat. Nos. 3,894,673 and 4,018,576. The disposition of the abrasive 105 on the wires 102 may depend upon the particular embodiment of the vascular occlusion material removal device.

In some embodiments, after the wires 102 are coated with the abrasive 105, a radiopaque material, such as gold, platinum, a radiopaque ink and the like, may be placed over the abrasive coated wires 102 to render the removal element 16 radioscopically visible. In still other embodiments, the abrasive coated wires 102 may be further coated with a low friction substance, such as nickel, a nickel plating infused with a fluoropolymer and the like. If nickel is used, a well known electroless plating process may be used to apply the nickel to the removal element 16. If a fluoropolymer infused nickel plating, such as nedox, is used, then this plating may be applied to the removal element 16 by the process performed by General Magnaplate Texas of Arlington, Tex. Other embodiments of the removal element 16 may not include an abrasive 105. In these embodiments, the wires 102 may be substantially ribbon-like in configuration. These ribbon-like wires are axially twisted and then braided to form the removal element 16. The edges of the twisted ribbon-like wires act substantially similarly to the abrasive 105 to remove occlusion material.

The wires 102 are preferably made from a super-elastic or shape memory metal alloy, such as nitinol and the like, which allows the wires 102 to recover strains greater than those recoverable by other metals. This increased strain recovery allows the wires 102 to resist permanent deformation during repeated expansions and contractions as well as during contact with vascular occlusion material. The use of super-elastic alloys for the wires 102 facilitates return of the material removal element 16 to its original low profile, contracted condition, which also makes intravascular navigation of the material removal element 16 easier and facilitates retention of vascular occlusion material within the material removal element 16. In an exemplary construction, the expandable material removal element 16 and the catheter assembly 14 as a whole have a sufficiently low profile to allow insertion of the catheter assembly 14 and the material removal element 16 through a conventional 7 French guide catheter.

A proximal annulus 104 is attached to the distal end 98 of the inner coil 94 by suitable means, such as an adhesive, solder, braze or a weld, and the proximal ends of the braided wires 102 are attached to the outer surface of the proximal annulus 104 by similar means. Thus, the braided wires 102 comprising the material removal element 16 rotate conjointly with the drive shafts 26 and 92 and the proximal annulus 104 under the influence of forces generated by the motor 24. The distal ends of the wires 102 are attached to a distal annulus 106, which may be made of a metal. In an exemplary embodiment, the distal annulus 106 is a hypotube, such as a 304 stainless steel 21XX hypotube available from Micro Group, Inc. of Medway, Mass., and the wires 102 are brazed to the distal annulus 106 with a Turbo braze paste available from Turbo Braze Corporation of Union, N.J. The wires 102, proximal annulus 104, and the distal annulus 106 are radioscopicly visible when the wires 102 are attached to the annuluses 104 and 106. The distal annulus 106 is provided with a substantially frusto-conical or tapered cutting surface 108 located distally of the point of attachment of the wires 102 so that the distal annulus 106 can act as a cutting burr, which may be useful in creating a pilot hole through tight, constricted vascular occlusions. The cutting surface 108 may also be coated with an abrasive 105, such as the diamond grit or synthetic abrasive disclosed earlier. It is also envisioned that the cutting surface 108 may have an auger-like configuration.

The braided wires 102 of the material removal element 16 define a hollow interior which can ingest or capture vascular occlusion material, as will be discussed in greater detail below. Abrasive 105 on the portions of the wires 102 facing the hollow interior may facilitate retention of the captured occlusion material within the hollow interior. In addition, the dimensions of the hollow interior are sufficient to accept a distal portion of the guidewire 42. Specifically, an aperture 110 is provided in the distal annulus 106 so that the guidewire 42 can be inserted therethrough and into the hollow interior of the material removal element 16. From there, the guidewire 42 can be inserted through the proximal annulus 104 into the hollow drive shaft 92, the drive shaft 26, the motor 24, and through the inner sheath 40, the outer sheath 58, and the guidewire lock mechanism 50. To traverse this distance, the guidewire 42 may be of a length suitable for facilitating removal and replacement of the device 10 within a patient, or may be extendable, and may be coated with a lubricous or a low friction substance, such as a fluoroploymer or a fluoropolymer-loaded nickel plating, to facilitate force transfer from the guidewire 42 to the distal end of the material removal element 16. The removal device 10 can also be exchanged intravascularly according to the methods disclosed in the co-pending U.S. patent application of Mazzola et al., Ser. No. 07/789,183, filed on Nov. 8, 1991. That application is assigned to the assignee of the present invention. and the disclosure thereof is incorporated herein by reference.

A distal end of the guidewire 42 includes a bearing surface 112, which can have one of several embodiments (FIGS. 6 through 9), which is fixedly attached to the guidewire 42. For example, the bearing surface 112 may be a short tube, a bearing or a bead 120 (FIG. 6) slipped onto the guidewire 42 having a smooth, low friction surface, a braze or solder fillet 122 (FIG. 7), or may be a centerless ground bump 124 (FIG. 8) on the guidewire 42. In some embodiments, the bearing surface 112 may be coated with a low friction substance, such as a fluoropolymer and the like. The bearing surface 112 is located at a proximal end of a radiopaque coil 114 which defines a distal-most end of the guidewire 42. The coil 114 may be made from platinum or other suitable substance, and, in an exemplary embodiment, has an axial length of about 3 cm and an outer diameter of about 0.014". The dimensions of the bearing surface 112 are larger than the corresponding dimensions of the aperture 110 in the annulus 106 so that the bearing surface 112 butts up against a distal end of the annulus 106, the significance of which will become more clear later. For example, the bearing surface 112 may define an outer diameter of about 0.016" and the aperture 110 may define an inner diameter of about 0.010" to 0.014". As stated above, the outer diameter surface of the guidewire 42 may be coated with a lubricous or low friction coating, such as fluoropolymer, a fluoropolymer-loaded metallic coating, a silicone dispersion, and the like, to minimize friction between the guidewire 42 and the drive shafts 26 and 92. This may be desirable because the guidewire 42 remains within the drive shafts 26 and 92 and is secured against axial movement by the wire lock mechanism 50 during operation of the occlusion material removal device 10.

With the basic structure of the occlusion material removal device 10 being thusly disclosed, a greater appreciation of the construction and benefits of the expandable material removal element 16 of the device 10 may be gained from the following discussion of the operation of the device 10. It is to be noted that this discussion is provided for illustrative purposes only.

The guidewire 42 is inserted intravascularly into the patient and navigated to the intravascular treatment site. If possible, the radiopaque coil 114 may be located through or distally of vascular occlusion material to be removed. A proximal end of the guidewire 42 is inserted through the distal annulus 106, and is guided through the more proximal portions of the removal device 10 until the distal end of the distal annulus 106 is proximate to the proximal end of the bearing surface 112 within the patient's vasculature. This procedure can be used if the guidewire 42 has sufficient length, i.e. is of exchange length. For shorter guidewires 42, the guidewire 42 can be pre-loaded into the removal element 16, and then the guidewire 42 and the element 16 can be conjointly inserted into the patient's vasculature. Sufficient length of the guidewire 42 can be positioned distally of the removal element 16 to facilitate intravascular navigation thereof.

The material removal element 16 is inserted into the patient's vasculature over the guidewire 42 while in the contracted position illustrated in FIG. 4. In an exemplary method of use, the removal device 10 is inserted into the patient's vasculature through a guide catheter or an introducer sheath in common fashion. If such a guide is used, then a fluid seal may be provided between the guide catheter and the device 10 to limit blood loss from the patient due to axial shifting of the device 10 with respect to the guide catheter. Thus, back flow of blood or other bodily fluids through a lumen between the guide catheter and the removal device 10 can be limited.

As shown, the axial distance between the distal end 98 of the inner coil 94 and the proximal end of the bearing surface 112 can be sufficient to allow the braided wires 102 comprising the material removal element 16 to completely axially relax or expand, thereby causing the material removal element 16 to contract radially. The proximal end of the bearing surface 112 may not contact the distal end of the distal annulus 106 when the material removal element 16 is in this contracted position. When in the contracted position, the material removal element 16 defines a low profile and an outer diameter slightly larger than the outer diameter of the drive shaft 92. This low profile facilitates intravascular navigation of the material removal element 16.

The removal element 16 is positioned adjacent the occlusion material to be removed. With some embodiments, the coil 114 of the guidewire 42 may have to be located across the occlusion, but it is envisioned that other embodiments may not require this. If the treating physician wishes to shift the material removal element 16 towards the expanded condition illustrated in FIG. 5, then the physician moves the guidewire 42 proximally as described above with reference to the guidewire lock mechanism 50 and the material removal element expansion control mechanism 52. As the treating physician moves the guidewire 42 proximally, the length of the guidewire 42 disposed within the patient's vascular system is reduced. Correspondingly, the axial distance between the bearing surface 112 and the distal annulus 106 decreases until the proximal end of the bearing surface 112 engages the distal end of the distal annulus 106. The guidewire 42 is moved progressively proximally and the axial distance between the distal annulus 106 and the distal end 98 of the inner coil 94 decreases. The braided wires 102 comprising the expandable material removal element 16 are axially compressed, thereby causing the material removal element 16 to expand radially.

Once the material removal element 16 is expanded to the desired degree, which can be positively verified by checking the scaling means 59 or 79 on the drive assembly 12, the thumb pad 66 of the material removal element expansion control mechanism 52 is released and now maintains the expanded position of the material removal element 16. The degree of expansion of the removal element 16 may also be positively verified by radioscopic techniques, i.e. if the particular embodiment of the removal element 16 is radioscopically visible. If the physician wishes to radially contract the material removal element 16, then he moves the guidewire 42 distally, as described hereinabove. By suitable manipulation of the guidewire 42, the guidewire lock mechanism 50, and the material removal element expansion control mechanism 52, the material removal element 16 can take on a number of different configurations and sizes, thereby changing the cutting profiles or characteristics of the material removal element 16 without having to remove the material removal element 16 from the patient's vasculature. This can provide the treating physician with greater flexibility in performing intravascular treatments, and may possibly reduce the cost of an intravascular procedure because multiple pieces of equipment need not be used.

While an expandable intravascular removal element 16 is highly desirable for the reasons discussed earlier, it may be desirable to limit the maximum size of these intravascular elements 16. It may be desirable not to overexpand the expandable removal elements 16. While some means for positively limiting radial expansion of the expandable intravascular removal element 16 have been detailed hereinabove, it may be desirable to provide additional safety mechanisms. For instance, it is to be noted that the expansion of the material removal element 16 shown in FIGS. 1, 4, and 5 is limited by contact between a proximal end 118 of the distal annulus 106 and the distal end 98 of the inner coil 94. The embodiments of the invention illustrated in FIGS. 6 through 9 provide constructions of removal element expansion limiting means which are included within the expandable elements 16 themselves. In addition, these Figures show some alternative constructions for the bearing surface 112, as indicated earlier.

Figure 6:
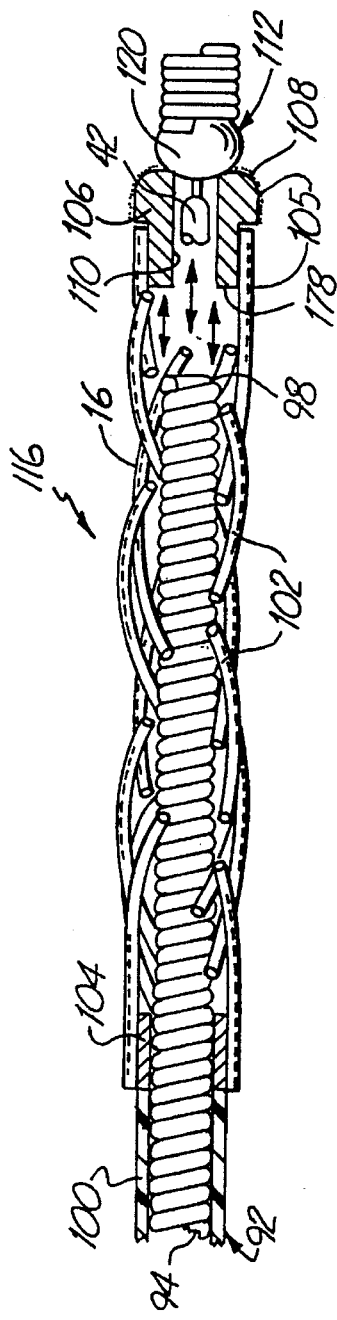
FIG. 6 is an enlarged, partially sectioned side elevational view of an alternative embodiment of the distal portion of the removal device of FIG. 1.

In the construction 116 of FIG. 6, the distal end 98 of the inner coil 94 extends through and distally of the proximal annulus 104 and into the hollow interior of the material removal element 16 defined by the braided wires 102. This is the currently preferred embodiment of the material removal element radial expansion limiting means. The distal end 98 of the inner coil 94 extends into the interior of the material removal element 16 a specific, predetermined distance which limits the radial expansion of the braided wires 102 by a corresponding distance. In other words, the proximal end 118 of the distal annulus 106 of the construction 116 can travel a maximum distance smaller than the distance traveled by the proximal end 118 of the distal annulus 106 of the embodiments of FIGS. 1, 4, and 5 upon maximum proximal movement of the bead 120 and the guidewire 42. Contact between the proximal end 118 of the distal annulus 106 and the distal end 98 of the inner coil 94 positively limits axial compression and radial expansion of the material removal element 16. Once the proximal end 118 engages the distal end 98, the removal element 16 cannot be further axially compressed because the guidewire 42 and the bead 120 cannot be moved further proximally. Thus, the material removal element 16 of the construction 116 can radially expand a predetermined maximum distance smaller than the maximum distance of radial expansion of the material removal element 16 of the embodiments of FIGS. 1, 4 and 5.

Figure 7:
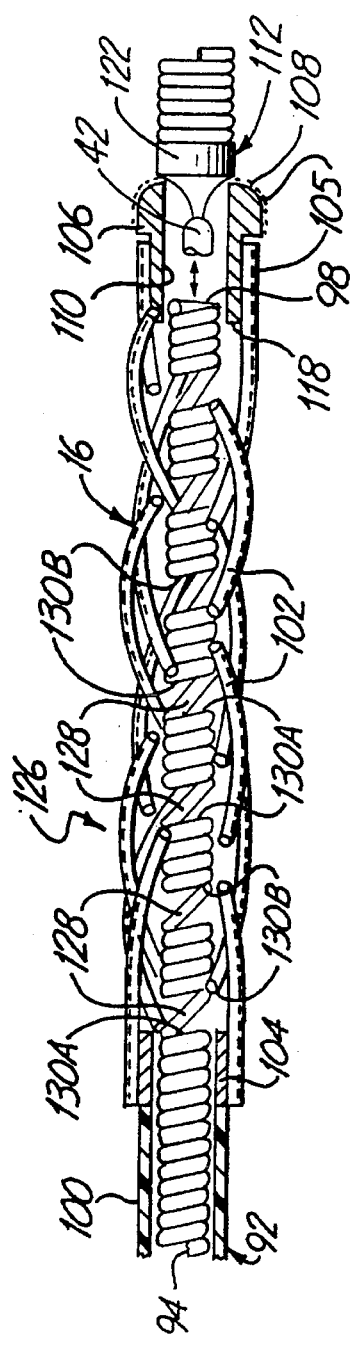
FIG. 7 is a view, similar to that of FIG. 6, of another embodiment of the distal portion.

Another construction 126 of the distal portion of the vascular occlusion material removal device 10 is shown in FIG. 7. This construction 126 utilizes material removal element radial expansion limiting means in the form of elongated windings 128 on a portion of the inner coil 94 that extend into the interior of the material removal element 16 in much the same manner as discussed hereinabove with respect to the construction 116. However, in this construction 126, the distal end 98 of the of the inner coil 94 is fixedly attached to the distal annulus 106 by solder, weld, braze or similar means. Thus, when the guidewire 42 is moved proximally and the fillet 122 engages the distal annulus 106, the expanded windings 128 within the hollow interior of the material removal element 16 are compressed until adjacent windings 130A and 130B on opposite sides of each of the expanded windings 128 contact each other. In this manner, the axial compression and the radial expansion of the braided material removal element 16 are positively limited by the sum of the distances between the adjacent windings 130A and 130B within the interior of the material removal element 16 when the material removal element 16 is in the relaxed, contracted position as shown.

Figure 8:
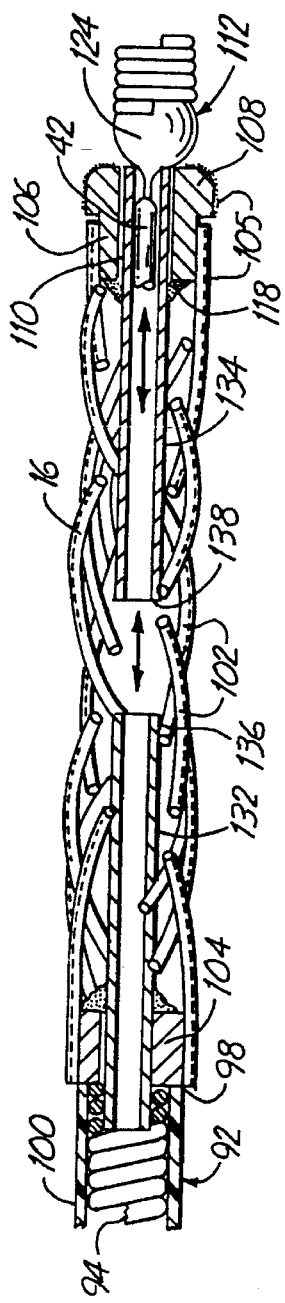
FIG. 8 is a view, similar to that of FIG. 7, of an additional embodiment of the distal portion.

Yet another embodiment of the material removal element radial expansion limiting means is shown in FIG. 8. Here, the means takes the form of two tubes 132 and 134, such as hypotubes and the like. The tube 132 is fixedly attached to an inner surface of the distal-most windings of the inner coil 94 by suitable means, such as adhesive, solder, braze or weld, and is also attached by similar means to the proximal annulus 104. This insures proper torque transfer from the drive shaft 92 to the material removal element 16. The tube 132 extends into the hollow interior of the material removal element 16 a certain, predetermined distance to locate a distal end 136 of the tube 132 within the hollow interior.

The tube 134 is fixedly attached to the distal annulus 106 by similar means, and extends proximally into the hollow interior of the material removal element 16 to locate a proximal end 138 of the tube 134 within the hollow interior. Thus, the distal end 136 of the tube 132 is offset from the proximal end 138 of the tube 134 by a predetermined distance which limits axial compression of the radially expandable material removal element 16. The tubes 132 and 134 both have inner diameters sufficient for accepting the guidewire 42 therethrough so that the material removal element 16 of this embodiment radially expands in the same manner as the other embodiments. As the guidewire 42 and the bump 124 move proximally, the bump 124 engages the distal annulus 106 and forces the distal annulus 106 and the tube 134 proximally. The braided wires 102 expand radially until the distal end 136 of the tube 132 contacts the proximal end 138 of the tube 134. This contact positively limits radial expansion of the material removal element 16. Thus, the lengths of both tubes 132 and 134 and the distance between the distal end 136 and the proximal end 138 determine the maximum radial expansion of the material removal element 16.

An additional embodiment of the material removal element radial expansion limiting means is contained in the construction 140 of FIG. 9. Here, the tube 134 is eliminated and the tube 132 is elongated with respect to the embodiment of FIG. 8. When the material removal element 16 is expanded fully, the proximal end 118 of the distal annulus 106 engages the distal end 136 of the tube 132. Thus, the length of the tube 132 and the distance between the distal end 136 of the tube 132 and the proximal end 118 of the distal annulus 106 within the hollow interior of the material removal element 16 determine and positively limit the maximum radial expansion of the material removal element 16.

In some cases, it may be desirable to perform balloon angioplasty in conjunction with vascular occlusion material removal. Because of this desire, another embodiment of the invention, an expandable intravascular occlusion removal device 142, is provided and is shown in FIG. 10. The removal device 142 is substantially similar to the removal device 10, except for the differences noted in the following paragraphs, hence the like reference numerals for similar structures. While the removal device 142 is illustrated as having the lock knob 54 and the thumb pad 66, it is to be remembered that the elements of the various embodiments of the invention can be combined in any desired fashion.

The removal device 142 includes a manifold assembly 144 and a catheter assembly 146 which differ from the catheter assembly 14 and the manifold assembly 22. Specifically, the manifold assembly 144 includes a third port 148 located distally of the port 82. The port 148 is connectable with a suitable source of fluid, not shown, but known in the art, for supplying the catheter assembly 146 with fluid to dilate a dilating member 158 for performing balloon angioplasty. The port 148 is located distally of a proximal end 150 of the catheter assembly 146.

The catheter assembly 146 includes a catheter sheath 152 having at least two lumens: a drive shaft lumen 154 and a fluid inflation lumen 156. The drive shaft 92 extends through the drive shaft lumen 154 from the distal end 34 of the drive shaft 26 to the proximal annulus 104, and the drive shaft lumen 154 can be utilized for infusion and aspiration in much the same manner as the catheter sheath 90 can. The drive shaft lumen 154 extends substantially the entire length from the manifold assembly 144 to the proximal annulus 104.

A dilating member 158, constructed substantially similarly to an angioplasty balloon, is located on the catheter assembly 146 offset proximally of a distal end 160 of the catheter assembly 146 and the distal end of the drive shaft lumen 154. The inflation lumen 156 extends from the port 148 to a proximal end 162 of the dilating member 158 and conveys fluid from the fluid source, conventionally referred to as an inflation device, to and from the dilating member 158, thereby causing the dilating member 1.58 to inflate and deflate. To facilitate intravascular location of the dilating member 158, a radiopaque marker band 164 is provided on the outer surface of the drive shaft lumen 154, thereby rendering the intravascular portion of the dilating member 158 radioscopically visible to a treating physician. Intravascular inflation of the dilating member 158 provides added stability to the distal portion of the removal device 142 during operation thereof, while also allowing the treating physician to occlude blood flow through the vascular lumen being treated and further allowing the physician to perform balloon angioplasty if desired. With the removal device 142 it is possible for a treating physician to cut, remove, and/or angioplasticly displace vascular occlusion material while only using a single piece of equipment.

Figure 12:
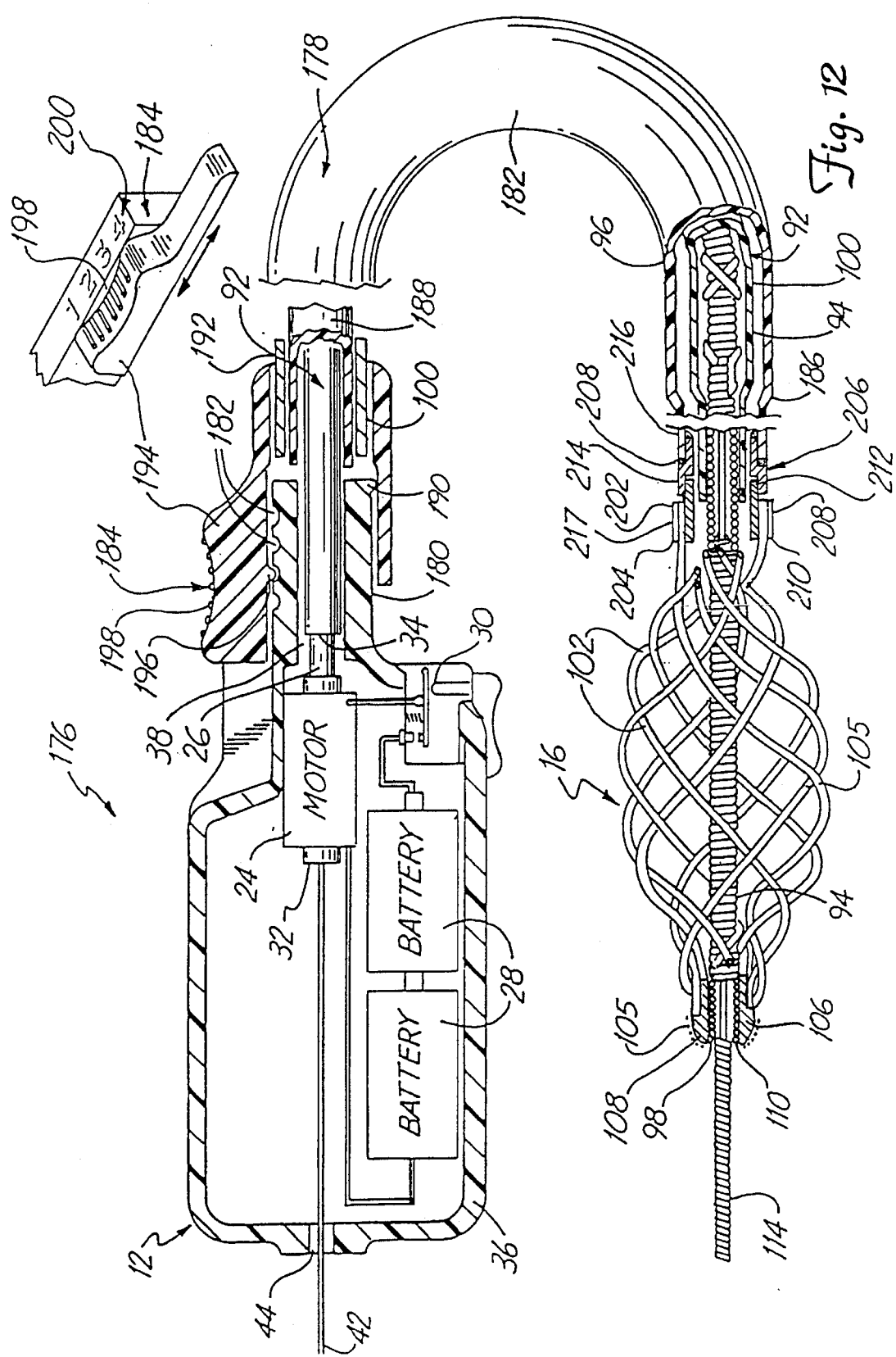
FIG. 12 is a sectional view of yet another embodiment of an expandable occlusion material removal device with the removal element in an expanded position.

Yet another embodiment 176 of an expandable intravascular occlusion material removal device is illustrated in FIG. 12. This embodiment 176 is substantially similar to the devices 10 and 142 described hereinabove, except for the differences detailed below, hence the like reference numerals for similar structures. The device 176 uses the same material removal element 16 and substantially the same drive assembly 12 as described earlier. However, because the device 176 does not use the guidewire 42 to move the removal element 16 between the contracted and the expanded positions, certain modifications can be made to the drive assembly 12. With the removal device 176, the removal element 16 is moved between the expanded position of FIG. 14 and the contracted position of FIG. 13 by axial movement of a catheter assembly 178 with respect to the drive shaft 92.

The drive assembly 12 comprises the housing 36 containing the motor 24, the power source 28, and the control switch 30. The housing 36 may be formed from a suitable material, such as polycarbonate, polyethylene or the like. In an exemplary embodiment of the removal device 176, the drive motor 24 may be a direct current micromotor, such as those disclosed hereinabove, which can produce a start up torque of about 2.6 ounce-inch and a no-load torque of about 0.015 ounce-inch. The drive motor 24 may have a speed range of about 5,000 to about 100,000 revolutions per minute, with a speed of about 20,000 revolutions per minute being the currently preferred operating speed of the device 176.

The drive motor 24 has the hollow drive shaft 26 so that the guidewire 42 can pass therethrough, thereby allowing the removal device 176 to be delivered over the guidewire 42. In an exemplary embodiment, the guidewire 42 may be substantially similar to guidewires used for percutaneous transluminal coronary angioplasty, although other guidewires may also be used. In some embodiments, at least a portion of the guidewire 42 may be coated with a silicone impregnated or fluoropolymer infused nickel material, such as nedox, or a nickel-silver alloy, such as nikasil and the like, to reduce friction between the guidewire 42 and the inner coil 92. If desired, a structure similar to that provided by the inner sheath 40 or the outer sheath 58 may be provided between the proximal end 32 of the drive shaft 26 and the aperture 44 in the housing 36 to direct the guidewire 42 from the proximal end 32 of the drive shaft 26 to the aperture 44. In addition, the guidewire lock mechanism 50 illustrated in FIGS. 1 through 3 and 10 may also be provided, if desired, adjacent the aperture 44 to fix the guidewire 42 with respect to the removal device 176.

The distal end 34 of the drive shaft 26 extends through the aperture 38 in the housing 36 and is connected by suitable means, such as solder, braze and the like, to the proximal end of the drive shaft 92. A seal may be provided adjacent the aperture 38 through which the drive shaft 26 sealingly passes to limit fluid flow into the housing 36. Another seal may be provided within the drive shaft 26 adjacent the aperture 38 through which the guidewire 42 can sealingly pass to further limit fluid flow into the housing 36. While this embodiment 176 is shown in FIG. 12 as not including a manifold assembly, it is to be recognized that the embodiment 176 can employ a manifold assembly, such as the manifold assemblies 22 (FIG. 1) or 144 (FIG. 10). The addition of a manifold assembly, possibly along with addition of appropriate lumens and other structures in the catheter assembly 178, can enable the removal device 176 capable of providing irrigation, drug delivery, aspiration, etc. The removal device 176 can also include the dilation member 158.

The housing 36 includes a shoulder member 180 extending from the housing 36 and surrounding the aperture 38 and the portion of the drive shaft 26 extending distally of the aperture 38. The shoulder member 180 may be substantially cylindrical in shape. A portion of the outer surface of the shoulder member 180 includes threads or grooves 182, the significance of which will be discussed later, which extend substantially diametrically inward on the outer surface of the shoulder member 180. The grooves 182 are part of a removal element expansion control mechanism 184 for positively moving the removal element 16, located at a distal end of the drive shaft 92, between the contracted and expanded positions.

In an exemplary embodiment, the inner coil 94 may be a tri-filar coil of 0.005" diameter 304 stainless steel wire. The inner coil 94 may have an inner diameter of about 0.0165" and an outer diameter of about 0.0265". These dimensions allow the removal device 176 to be delivered over a guidewire 42 having a diameter of about 0.010" to 0.014". The choice of guidewire 42 outer diameter may depend upon utilization of aspiration. The axial length of the inner coil 94 may be about 140 cm, but other lengths are possible if desired. The inner coil 94 may be provided with various pre-load options, e.g. to reduce torsional flexibility and increase torsional rigidity of portions of the drive shaft 92, by known methods. The pre-load options of the inner coil 92 are chosen such that the inner coil 94 can efficiently deliver torque to the removal element 16 while also being able to navigate through a vascular lumen over a guidewire 42 and to effectively move the removal element 16 between the contracted and expanded positions. For instance, by pre-loading or axially twisting a wire during formation of a portion of the coil 92, that twisted portion can have increased rigidity as compared to another portion of the coil 92. The portion having increased rigidity can facilitate pushability of the removal device 176 while the other portion of the coil 92, having less rigidity, can facilitate trackability of the device 176.

The coating 100 may be provided, e.g. in the form of a 0.002" thick heat shrink fluoropolymer tube which is applied to the outer diameter surface of the drive shaft 92 along its entire axial length. However, the coating 100 may not cover the distal end 98 of the inner coil 94, the significance of which will become clear later. The length of the coating 100 may be chosen to determine the location of an irrigation port on a distal portion of the drive shaft 92. In an exemplary embodiment, the braid 96 may be formed from eight 0.002" diameter 304 stainless steel wires braided at about 40 pics per inch. The braid 96 may be about 100 cm long, and is tensioned and attached to the outer diameter surface of the inner coil 94 as discussed earlier. Because the braid 96 may not be as long as the inner coil 94, the outer diameter or profile of the drive shaft 92 reduces distally of a distal end 186 of the braid 96. Thus, the profile of the portions of the catheter assembly 178 distal of the distal end 186 can also be correspondingly reduced. This reduced profile can increase the accessibility of some vascular occlusions to the removal device 176.

The catheter assembly 178 includes a catheter shaft 188 which surrounds the length of the drive shaft 92 substantially from the distal end 34 of the drive shaft 26 to the proximal end of the removal element 16. In an exemplary embodiment, the catheter shaft 188 may be a 0.002" thick tube of a suitable polymeric material, such as KYNAR and the like, and may be about 135 cm long. The catheter shaft 188 may be provided in other lengths. For example, the proximal portion of the catheter shaft 188, measuring about 100 cm, may have an outer diameter of about 1.3 mm, while a distal portion thereof, measuring about 35 cm, may have an outer diameter of approximately 1 mm. The juncture between the proximal and distal portions of the catheter shaft 188 is adjacent the distal end 186 of the braid 96 or the outer coil of the drive shaft 92.

A proximal end 190 of the catheter shaft 188 is attached to an inner diameter surface of a strain relief robe 192 by a suitable adhesive, such as a cyanoacrylate, urethane or similar adhesive. The strain relief tube 192 may be substantially cylindrical and may have a thickness of about 0.003" and an axial length of about 4 cm. The strain relief tube 192 may be made from a suitable polymeric material, such as a nylon-polyether blend like PEBAX (France) and the like. The strain relief tube 192 is of suitable construction for absorbing strains on the catheter assembly 178.

The outer diameter surface of the strain relief tube 192 is attached to an adjustment member 194 by a suitable adhesive, such as a cyanoacrylate, a urethane, or the like. The adjustment member 194 may be made from a suitable polymeric material, such as polycarbonate, polyurethane and the like, and may be substantially cylindrical in configuration. The adjustment member 194 has an inner diameter sufficient so that the adjustment member 194 can surround the drive shaft 92, the shoulder portion 180, the catheter shaft 188 and the strain relief tube 192. A suitable seal may be disposed between the outer surface of the shoulder portion 180 and the inner surface of the adjustment member 194 to limit fluid from flowing between the shoulder portion 180 and the adjustment member 194.

The adjustment member 194 cooperates with the shoulder portion 180 to form the expansion control mechanism 184 for positively moving the removal element 16 between the contracted position of FIG. 13 and the expanded position of FIG. 14. Specifically, at least one tab 196 extends substantially diametrically inward from the inner surface of the adjustment member 194 towards the outer surface of the shoulder portion 180. The tab 196 has a configuration complementary to the configuration of the grooves 182 on the outer surface of the shoulder portion 180 so that the tab 196 can be inserted into and mate with the grooves 182. The tab 196 can be shifted out of one groove 182 and into an adjacent groove 182 by application of a suitable force to the adjustment member 194. To facilitate shifting of the tab 196 between adjacent grooves 182, the adjustment member 194 has an actuating portion 198 having a configuration adapted for accepting force manually applied by a treating physician.

By applying an appropriate force to the actuating portion 198, the physician can move the tab 196 between adjacent grooves 182 on the shoulder portion 180. The adjustment member 194 moves in unison with the tab 196, which also causes corresponding movement of the strain relief robe 192 and the catheter shaft 188. Because the tab 196 and the adjustment member 194 move axially with respect to the grooves 182 and the shoulder portion 180 responsive to application of forces by the treating physician to the actuating portion 198, the catheter shaft 188 conjointly moves axially with respect to the drive shaft 92. Relative axial movement of the drive shaft 92 and the catheter shaft 188 causes corresponding movement of the removal element 16 between the contracted position of FIG. 13 and the expanded position of FIG. 14. If the grooves 182 are thread-like, relative axial movement of the drive shaft 92 and the catheter shaft 188 may be accomplished by rotation of the adjustment member 194 about the shoulder portion 180. Scaling means 200 is also provided on the expansion control mechanism 184 for giving the treating physician a visual indication of the position of the removal element 16. The position of the removal element 16 may also be verifiable by radioscopic visualization techniques. It is to be noted that, in some alternative embodiments of the removal device 176, the expansion control mechanism 184 may be constructed so that catheter shaft 188 may be selectively detached from the drive assembly 12.

The construction of the distal end of the removal device 176 is more clearly illustrated in FIGS. 13 and 14. The inner coil 94 of the drive shaft 92 extends through the entire axial length of the removal element 16. The distal end 98 of the inner coil 94 is attached to the distal annulus 106 within the aperture 110 by suitable means, such as braze, solder or the like, as discussed earlier with respect to attachment of the wires 102 to the annuluses 104 and 106. In this embodiment 176, however, it is to be recognized that the guidewire 42 does not have a bearing surface 112 and that the aperture 110 in the distal annulus 106 may be of sufficient size to allow withdrawal of the guidewire 42 therethrough. This is a distinction over the previously-discussed embodiments of the invention and is possible because the guidewire 42 is not used to move the removal element 16 between the collapsed position and the expanded position. However, in some circumstances, it may be desirable to have a guidewire 42 which cannot be withdrawn from the removal device 176 during operation thereof, such as when it is desirable to retain the removal element 16 on the guidewire 42. With this embodiment 176, it may not be necessary to have a non-occluded lumen within the vasculature of sufficient size to accept the coil 114 or distal portions of the guidewire 42 in order to remove occlusion material with the removal device 176.

Proximal ends 202 of the wires 102 are attached to an annular expansion bearing surface or member 204 by suitable means, such as a weld, braze, solder or the like. In an exemplary embodiment, the proximal ends 202 are brazed to the bearing member 204 with a Turbo braze paste available from Turbo Braze Corporation of Union, N.J. The bearing member 204 cooperates with a complementary bearing surface or member 206 attached to a distal end 208 of the catheter shaft 188 by a suitable adhesive, such as a cyanoacrylate, urethane, or other adhesive. In an exemplary embodiment, the bearing members 204 and 206 may comprise 21XX hypotubes formed from 304 stainless steel and available from Micro Group, Inc. of Medway, Mass.

The bearing members 204 and 206 have complementary configurations such that one member 204 or 206 can freely rotate within the other member 204 or 206. For instance, the bearing members 204 and 206 may be flared and necked-down, respectively, to facilitate relative rotation of the members 204 and 206. In the illustrated embodiment, the bearing member 204 has a relatively large outer diameter portion 210 and a relatively small outer diameter portion 212 with the portion 210 being located distally of the portion 212. The wires 102 are attached to the outer surface of the portion 210 and the bearing member 204 has a constant inner diameter to accept the inner coil 94. In some embodiments of the removal device 176, the bearing member 204 may be substantially cylindrical in configuration having constant inner and outer diameters. The bearing member 206 has a relatively large inner diameter portion 214 and a relatively small outer diameter portion 216 with the portion 214 being located distally of the portion 216. The outer diameter of the portion 216 is substantially equal to the inner diameter of the distal end 208 of the catheter shaft 188 to insure a firm connection between the catheter shaft 188 and the bearing member 206. The inner diameter of the portion 214 of the bearing member 206 is slightly larger than the outer diameter of the portion 212 of the bearing member 204. Thus, the portion 212 of the bearing member 204 is insertable into the portion 214 of the bearing member 206. Accordingly, when the motor 24 is energized, the bearing member 204 can rotate within the bearing member 206. In some embodiments of the device 176, a lubricous or low friction substance 217, such as a fluoropolymer, nedox and the like, may be coated onto the outer surface of the portion 212 and the inner surface of the portion 214, as well as other mating surfaces, to facilitate rotation of the bearing member 204 within the bearing member 206. It is to be appreciated that, in other embodiments, the bearing member 206 may rotate within the bearing member 204. Any construction of the bearing members 204 and 206 is possible as long as the proximal end of the removal element 16 is capable of free-wheeling movement with respect to the catheter shaft 188.

Further structural details of the embodiment 176 may become more clear with reference to the following discussion of the operation thereof. Again, it is to be noted that the elements of each of the embodiments 10, 142 and 176 of the invention may be combined in any suitable fashion to produce a vascular occlusion material removal device having desired properties. For instance, it is to be recognized that any of the embodiments of the material removal element expansion limiting means may be included with the removal device 176. The removal device 176 functions substantially similarly to the removal devices 10 and 142 disclosed earlier except for the method of moving the removal element 16 between the contracted and expanded positions. Thus, the discussion of operation of the removal device 176 will be limited to the method of expanding the removal element 16.

It is to be noted that, in the contracted position, the adjustment member 194 is positioned closest to the drive assembly 12. With the removal element 16 in the contracted position of FIG. 13, a treating physician wishing to move the removal element 16 towards the expanded position (FIG.

14) applies a suitable force to the actuation portion 198 of the adjustment member 194. This force removes the tab 196 from the proximal-most groove 182 and shifts the tab 196, along with the adjustment member 194, distally along the shoulder portion 180. As the adjustment member 194 moves distally along the shoulder portion 180, the strain relief tube 192 and the catheter shaft 188 also conjointly move axially with respect to the drive shaft 92 in the distal direction.

Because the distal end 98 of the drive shaft 92 is fixed to the distal annulus 108 and the removal element 16, distal axial movement of the catheter shaft 188 with respect to the drive shaft 92 reduces the axial distance between the distal annulus 108 and the bearing members 204 and 206. The bearing member 206 transmits force from the catheter shaft 188 to the bearing member 204, and, from there, to the wires 102. Opposite ends of the braided wires 102 are attached to the distal annulus 108 and the bearing member 204, respectively, such that reduction of the axial distance between the distal annulus 108 and the bearing member 204 causes the wires 102 to bow radially outwardly from the inner coil 94 of the drive shaft 92.

In this manner, the removal element 16 moves between the contracted position of FIG. 13 and the expanded position of FIG. 14. Because the removal element 16 moves between the contracted and expanded positions responsive to movement of the catheter shaft 188, the scaling means 200 provides the treating physician with a visual indication of the diameter defined by the wires 102. It is to be noted that this removal element 16 expanding movement of the catheter shaft 188 can also be viewed, from a suitable reference frame, as the drive shaft 92 shifting with respect to the removal element 16. Therefore, it is equally valid to refer to expansion of the removal element 16 responsive to movement of the drive shaft 92 or the catheter shaft 188 with respect to the removal element 16.

Once the desired positioning of the removal element 16 is achieved, the treating physician releases the actuation portion 198, and the tab 196 comes to rest in a groove 182. This locks the removal element 16 in the desired position. If it is desired to move the removal element 16 back towards the contracted position, the above-discussed steps are repeated, but the direction of the force applied to the actuating portion 198 of the adjustment member 194 is reversed to cause movement of the adjustment member 194 and the catheter shaft 188 proximally towards the drive assembly 12.

Figure 17:
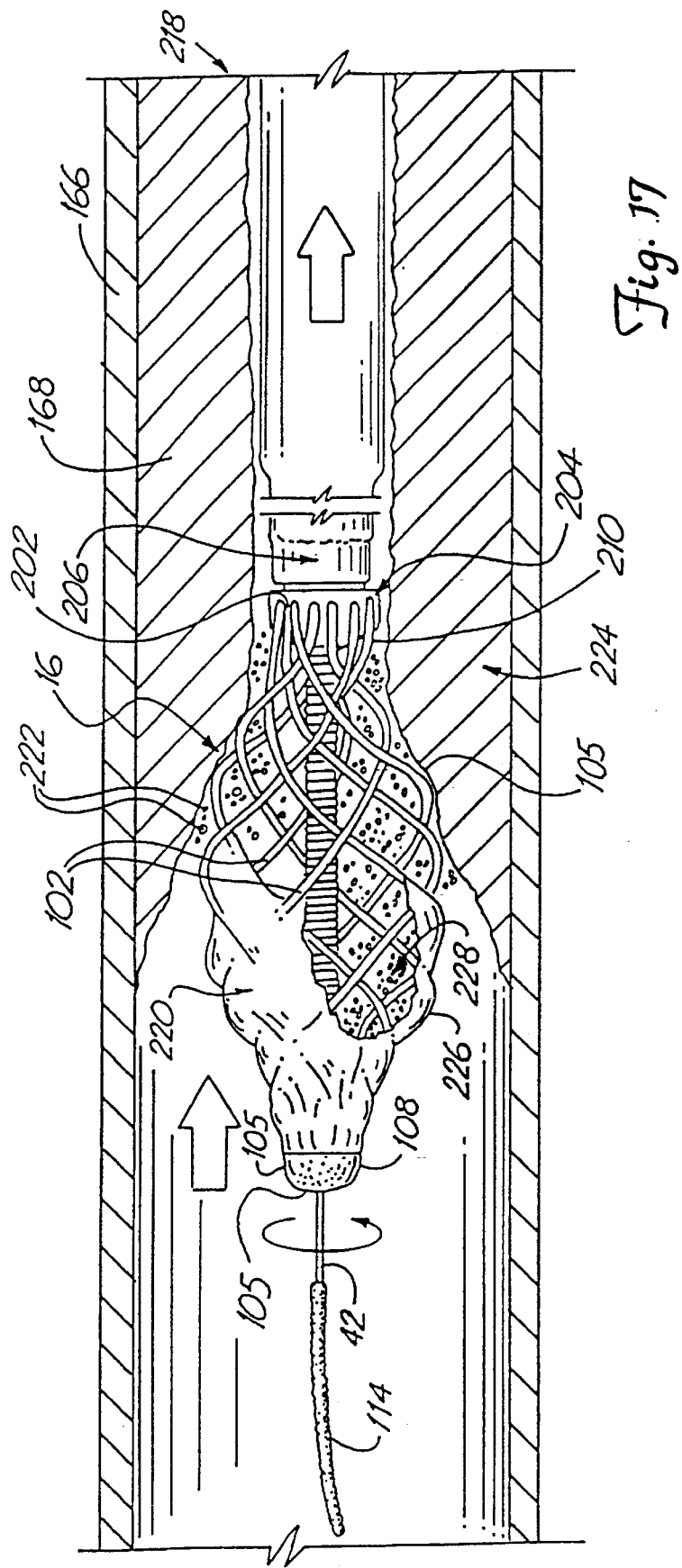
FIG. 17 is a sectional view of an alternative embodiment of a vascular occlusion material removal device expanded distally of an occlusion and moved towards the occlusion to remove occlusion material.

Yet still a further embodiment 218 of the invention is illustrated in FIG. 17. The embodiment 218 is substantially similar to the embodiment 176 except for the differences noted below, hence the like reference numerals for similar structures. The embodiment 218 differs from the embodiment 176 in that the removal element 16 includes a collection portion 220 for collecting occlusion particulate 222 removed from a vascular occlusion 224. The collection portion 220 may be provided with the removal devices 10 and 142 as well. Also, it is to be recognized that, while the collection portion 220 is illustrated in FIG. 17 as being disposed on a distal end of the removal element 16, the collection portion 220 may alternatively be disposed on the proximal end of the removal element 16. Generally, the collection portion 220 is located on the removal element 16 at a position where particulate 222 from the occlusion 224 may be collected, and thus, the disposition of the collection portion 220 may depend upon whether the removal element 16 is to be moved proximally or distally against the occlusion 224.

In the illustrated embodiment of the removal device 218, the collection portion 220 is disposed on a distal portion of the removal element 16 so that particulate 222 removed from the occlusion 224 will naturally move towards the collection portion 220 under the influence of fluid flow through the vasculature. Movement of particulate 222 into the collection portion 220 can further be insured by utilizing the removal device 218 to remove occlusion material while being moved proximally across the occlusion 224, viz. in a direction opposite to the direction of fluid flow through the lumen. This method of operation of the removal device 218 will be discussed in greater detail later. In an alternative embodiment of the removal device 218, fluid may be provided through the drive shaft 92 and/or the catheter shaft 188 so that this fluid flow can direct particulate 222 into the collection portion 220. The fluid may be filtered by a retention member or coating 226 forming the collection portion 220 and may be able to exit the collation portion 220 through the aperture 110 in the annulus 106. Because the collection portion 220 is disposed on the distal portion of the removal element 16, it may not be desirable to place abrasive 105 on the portions of the wires 102 forming the collection portion 220.

In an exemplary embodiment of the removal device 218, the collection portion 220 may be formed by a retention member in the form of a polymeric coating 226, such as polyurethane, Pellathane™ (Dow Chemical) and the like, disposed on the distal portion of the removal element 16. The polymeric coating 226 may be applied to the wires 102 in a number of ways, such as by dipping the removal element 16 in the polymer, spraying the polymer onto the wires 102 with, for example, an air brush, directly applying the polymer to the wires 102, etc. The coating 226 is applied to the wires 102 such that at least the outer surfaces of the wires 102 are coated, and so that, when the removal element 16 is moved into the expanded position, the coating 226 will stretch across and cover spaces between adjacent wires 102. In this manner, the coating 226 forms a boundary of a particulate collection chamber 228 located at the interior of the removal element 16. It is to be noted that, in some embodiments of the removal device 218, the collection portion 220 may not be formed from a polymeric coating 226, but may be formed from a fabric or filter-like material, such as GORTEX and the like, or a polypropylene screening material. In general, the collection portion 220 is formed from any suitable material having apertures whose diameters measure about 5 microns. These apertures may allow blood or other fluid to pass distally through the collection portion 220 while /retaining occlusion particulate 222 larger than 5 microns within the collection portion 220. In some embodiments, the collection portion 220 may be able to occlude fluid flow. These embodiments of the collection portion 220 may facilitate removal of occlusion particulate by aspiration because fluid would not flow beyond the collection portion 220. Thus, the scope of the claims is not to be limited by the above-discussed constructions of the collection portion 220.

The various embodiments 10, 142, 176 and 218 of the present invention also provide a number of methods for performing intravascular treatments, such as removing or displacing vascular occlusion material. These methods comprise a plurality of steps, some of which have been discussed in detail already, so the following discussion of the methods will simply refer back to those detailed discussions, instead of restating them, where appropriate. As with the mechanical elements of the embodiments 10, 142, 176 and 218 of the invention, the steps of the methods may also be combined in suitable fashion to perform a desired treatment.

The expandable intravascular occlusion material removal device 10, 142, 176 or 218 is inserted into the patient's vascular system through a suitable puncture or other access site, such as via the femoral artery, in well known fashion. At this point, the expandable material removal element 16 is in the radially contracted position shown in FIG. 4. Because the removal device 10, 142, 176 or 218 has a low profile when the material removal element 16 is in the contracted position, the intravascular portion of the removal device 10, 142, 176 or 218 can be inserted through a conventional 7 French guide catheter, well known to those having ordinary skill in the relevant art. The removal device 10, 142, 176 or 218 is moved over the medical guidewire 42, which has been previously positioned in proximity to the intravascular treatment site, until the distal end of the annulus 106 is adjacent the proximal end of the bearing surface 112, if present, as discussed hereinabove. Now, the expandable material removal element 16, currently in the contracted position, is located in close proximity to the vascular occlusion material to be removed thereby.

At any time, a fluid, such as saline, a drug therapy, heparinized saline, an oxygenated fluid, such as FLUOR-SOL, and the like, can be applied to the port 80 on the manifold assembly 22 or 144 from a suitable fluid source. The fluid flows through the port 80 and into the portion of the main lumen 78 located between the fluid seal 84 and 86, and from there, through the aperture 88 into the hollow interior of the drive shaft 92. The fluid flows along the axial length of the drive shaft 92 and passes into the hollow interior defined by the braided wires 102 of the expandable material removal element 16. The fluid can flow through spaces between adjacent portions of the braided wires 102 to infuse the intravascular treatment site with fluid. Alternatively, with the embodiment 176, the fluid may flow through the aperture 110 in the distal annulus 106. Also, the location at which the fluid exits the drive shaft 92 may be predetermined by appropriately choosing the length of the coating 100. This may provide for maintenance of fluid within a vascular lumen if aspiration is used.

At any time, another fluid to be infused into the patient, or a negative pressure to aspirate the intravascular treatment site may be applied to the port 82 from a suitable source. The fluid or the negative pressure is applied through the port 82 to the hollow interior of the catheter sheath 90, 152 or 188 and from there to the vascular lumen adjacent the distal end 18, 160 or 208 of the catheter assembly 14, 146 or 178, respectively. Because of the relative locations of the distal ends of the drive shaft 92 and the catheter sheath 90, 152 or 188, as discussed earlier, effective aspiration of the treatment site may be provided. This is important because some vascular occlusion material, such as certain types of thrombus, may be removed from a vascular surface or another occlusion simply by aspiration.

In some other embodiments of the removal device 10, 142, 176 and 218, aspiration may be provided by an impeller-like element operatively attached to the drive shaft 92 such that rotation of the drive shaft 92 and the impeller element generates a fluid flow within the vascular lumen, thereby causing particulate 222 to flow into the catheter sheath 90, 158 or 188. In other embodiments, multiple impeller-like elements may be attached to the shaft 92 at various locations along the longitudinal axis thereof.

If desired, the removal devices 10, 142, 176 or 218 may be delivered through another catheter, such as the guide catheter discussed earlier. If this is done, fluid may be provided through the drive shaft 92 and/or through the catheter sheath 90, 152 or 188. This fluid may generate a positive pressure within the vascular lumen. At the same time, a negative pressure may be provided through the guide catheter. This could produce a pressure differential within the vascular lumen which could force fluid and occlusion particulate 222 proximally through the guide catheter and out of the patient's body. This method may also be used to force fluid and occlusion particulate 222 proximally through the catheter sheath 90, 158 or 188. In still other embodiments, a dilation member may be provided at the distal end of the guide catheter, and/or another dilation member, similar to an angioplasty balloon may be located distally of the removal element 16. By intravascularly inflating both of these dilation members, the intravascular treatment site may be substantially isolated, which can facilitate particulate 222 removal.

With the expandable material removal element 16 being positioned with respect to the vascular occlusion material to be removed, the treating physician can expand the material removal element 16 to the desired degree by implementing the methods discussed earlier with respect to the guidewire lock mechanism 50 and the material removal element expansion control mechanism 52 for the embodiments 10 and 142, and with respect to the expansion control mechanism 184 for the embodiments 176 and 218. The material removal element 16 can be moved into a plurality of positions by variably expanding and/or contracting the material removal element 16. Thus, multiple material removal element 16 sizes, shapes, profiles and characteristics may be achieved with the use of a single occlusion material removal device 10, 142, 176 or 218. The controlled, incremental expansion and contraction of the expandable material removal element 16 can provide a treating physician with greater flexibility in performing intravascular treatments, as well as possibly reducing the costs of such treatments because multiple pieces of equipment need not be used. This is a significant improvement over some of the intravascular treatment devices of the prior art. In addition, the various constructions of the material removal element radial expansion limiting means may insure that the material removal element 16 is not over-expanded.

With the removal device 142, either before of after expansion of the expandable material removal element 16, the dilating member 158 can be inflated to a suitable pressure by application of a pressurized fluid to the port 148, as discussed above. The pressurized fluid flows through the port 148 and the lumen 156, and into the interior of the dilating member 158. The dilating member 158 expands sufficiently so that an outer surface thereof engages the interior surface of the vascular lumen. The dilating member 158 can be inflated to pressures on the order of 4 to 8 atmospheres and can center and stabilize distally-located portions of the removal device 142 during operation thereof. Inflation of the dilating member 158 can also be used to occlude blood flow through the vasculature being treated.

The removal device 10, 142, 176 or 218 is now ready to remove vascular occlusion material from a vascular surface or from a vascular occlusion by expansion and/or rotation of the expandable material removal element 16. It is to be noted that, because the expandable material removal element 16 is comprised of braided wires 102 which define spaces between adjacent wires 102, expansion of the material removal element 16 may not occlude fluid flow through the vascular lumen. For example, fluids infused into the vasculature by the device 142 at a location distally of the dilating member 158 can flow around and through the spaces between the braided wires 102 and continue through the patient's vasculature distally of the material removal element 16.

If the occlusion material were located radially above the material removal element 16, then appropriate expansion of the wires 102 can allow the abrasive 105 or other cutting surface on the wires 102 to bite into a portion of the occlusion material. This radial cutting of the wires 102 into the vascular occlusion material can cause a portion of the material to pass through spaces between adjacent wires 102 and be captured in the hollow interior of the material removal element 16 defined by the wires 102. The expansion of the braided wires 102 defines a radially directed cutting vector for severing occlusion material. The effectiveness of this radial cutting may depend upon the composition or hardness of the vascular occlusion material. If desired, the expandable material removal element 16 can be moved into the contracted position, thereby trapping occlusion material within the hollow interior defined by the braided wires 102. The material removal element 16 can be removed from the patient's vasculature if desired and the occlusion material will be retained within the hollow interior of the material removal element 16 because of the spring-like forces inherent in the wires 102. With the removal device 218, retention of occlusion material within the collection chamber 228 within the hollow interior of the braided wires 102 is enhanced by the coating 226. The captured material can be later retrieved for performing a biopsy or other procedure on the material.

Some occlusion material may not be susceptible to removal in this fashion. For instance, some occlusion material may be relatively hard or calcified, thereby making it rather difficult for the wires 102 to bite into the material upon expansion of the material removal element 16. If this is the case, then the material removal element 16 can be expanded such that the outer surfaces of the braided wires 102 contact the interior surface defined by the occlusion. In other words, the material removal element 16 is expanded to define a cutting diameter slightly larger than a non-occluded diameter of a particular portion of the vasculature. By expanding the diameter of the removal element 16 to a size slightly larger than the non-occluded diameter of the vascular lumen, more effective and more efficient removal of occlusive material is provided as compared to some prior art methods where a cutting element is expanded to define a diameter equal to that of the vascular lumen. The material removal element 16 is expanded and is locked in this expanded position according to the methods described earlier with respect to the guidewire lock mechanism 50 and the material removal element expansion control mechanism 52 for the embodiments 10 and 142, and with respect to the expansion control mechanism 184 for the embodiments 176 and 218. The maximum radial expansion of the material removal element 16 is limited by the radial expansion limiting means discussed hereinabove.

Once locked in the expanded position, the treating physician actuates the control switch 30, thereby energizing the motor 24. The motor 24 induces rotation of the drive shaft 26, which, in turn, causes the drive shaft 92 to rotate within the catheter sheath 90, 152 or 188. The material removal element 16 is also rotated conjointly with the drive shafts 26 and 92. The rotation of the material removal element 16 enables the sharp edges or abrasive 105 particles on the surfaces of the braided wires 102 to cut, abrade, ablate, or otherwise remove vascular occlusion material from a vascular lumen surface or a vascular occlusion.

Rotation of the braided wires 102 defines a cutting vector directed tangentially to the surface interface between a given wire 102 and the occlusion material. The removed occlusion material can pass through the spaces between adjacent wires 102 and be caught in the collection chamber 228 or the hollow interior defined by the braided wires 102 comprising the material removal element 16. This removed material can be trapped within the material removal element 16 upon contraction thereof, as described earlier, and subsequently removed from the patient's vasculature along with the material removal element 16. With the embodiment 218, the coating 226 can facilitate retention of particulate 222 within the chamber 228. Alternatively, the removed vascular occlusion material can be drawn into the interior of the catheter sheath 90 or 152 by means of negative pressure applied to the port 148. Thus, there are at least three ways by which removed vascular occlusion material can be carried away from the patient's vasculature.

After a sufficient amount of vascular occlusion material has been removed by rotation of the material removal element 16, the non-occluded diameter of the vascular lumen is enlarged, but further occlusive material may remain within the vascular lumen. It may be desirable to remove more occlusion material, thereby further enlarging the non-occluded diameter of the vascular lumen. To do this, the expandable material removal element 16 is further radially expanded, according to the steps of the method discussed earlier, to define a cutting diameter slightly larger than this second, non-occluded diameter of the vascular lumen. This process of expanding the cutting diameter of the material removal element 16 progressively—starting small and finishing large—can be repeated as often as necessary until a non-occluded diameter of the desired length is formed in the vascular lumen. This progressive cutting process allows for more efficient removal of the occluding material by always using a cutting diameter just slightly larger than the non-occluded diameter. The expandable nature of the material removal element 16 allows this process to be executed while utilizing only one intravascular device 10, 142, 176 or 218. Also, this process can be used in conjunction with moving the device 10, 142, 176 or 218 either distally or proximally against the occlusion.

It is possible that a particular vascular lumen might have more than one occlusion which may be located distally of a first occlusion. If this is the case, after sufficient material of the first occlusion is removed to revascularize that portion of the lumen, then the material removal element 16 can be repositioned intravascularly adjacent a second occlusion for removing its occluding material. To reposition the material removal element 16, the dilating member 158, if inflated, should be deflated. The material removal element 16 should also be moved into the contracted position. The material removal element 16, the dilating member 158 and the distal portion of the catheter assembly 14, 146 and 178 assume a low profile for facilitating intravascular movement of the removal device 10, 142, 176 or 218. The entire removal device 10, 142, 176 or 218 can now be freely repositioned for removing material from the second occlusion. It is envisioned that, in some embodiments of the invention, the drive shaft 92 and the cutting element 16 may be axially shiftable with respect to the catheter sheath 90, thereby facilitating intravascular repositioning of the removal element 16.

Once properly positioned adjacent the second occlusion, the material removal element 16 can be expanded as before and the same process of occlusion material removal can be performed. There may be some occlusions, however, which define a non-occluded diameter smaller than the outer diameter defined by the braided wires 102 in the contracted position. With the removal devices 176 and 218, the guidewire 42 may be withdrawn sufficiently such that the cutting surface 108 on the distal annulus 106 can engage and remove occlusion material. However, if the non-occluded diameter were large enough to accept the coil 114 of the guidewire 42 and the bearing surface 112, if present, then the occlusion material can still be removed by the material removal element 16. In this case, the coil 114 of the guidewire 42 and the bearing surface 112, if present, are passed through the non-occluded diameter sufficiently to bring the cutting surface 108 on the distal annulus 106 into contact with a proximal end of the occlusion. The cutting surface 108 has a configuration or an abrasive 105 coating which facilitates removal of vascular occlusion material upon rotation of the distal annulus 106. In addition, as the Figures show, the cutting surface 108 is tapered so that a relatively smaller cutting diameter encounters the occlusion material initially.

The motor 24 is energized, thereby rotating the material removal element 16 and the distal annulus 106, and the cutting surface 108 begins to bore through the occlusion material. The cutting action of the cutting surface 108 is directed substantially longitudinally or axially within the vascular lumen, and the cutting surface 108 can grind away occlusion material from the occlusion or the vascular surface thereby increasing the size of the non-occluded diameter in the vascular lumen. Of course, aspiration can be used to carry the removed material away from the patient. The treating physician can apply an axially directed force to the removal device 10, 142, 176 or 218 as the cutting surface 108 rotates to move the cutting surface 108 distally through the occlusion. Since the cutting surface 108 is tapered, a progressively larger cutting diameter is engaged against the vascular occlusion as the cutting surface 108 and the associated removal device 10, 142, 176 or 218 are moved distally within the vascular lumen. Thus, the cutting surface 108 also executes substantially the same occlusion material removal process described above by starting with a small cutting diameter and gradually increasing that diameter as progressively more occluding material is removed.

The cutting surface 108 is rotated against the occlusion and simultaneously advanced distally with respect to the occlusion to form an enlarged diameter pilot hole longitudinally through the occlusion. This process is illustrated in FIG. 15 with respect to the removal device 176. As more proximal portions of the cutting surface 108 encounter the occlusion material, the cutting surface 108 may cut occlusion material along vectors directed tangentially to the interface of the cutting surface 108 and the occlusion. It is to be noted that a proximal-most portion of the cutting surface 108 defines an outer diameter substantially equal to the outer diameter defined by the braided wires 102 when in the contracted position, as shown in FIG. 15. Thus, the pilot hole formed by the cutting surface 108 has dimensions sufficient for accepting the material removal element 16 in the contracted position. Therefore, once this pilot hole has been formed, the motor 24 can be stopped, which ceases rotation of the material removal element 16 and the cutting surface 108. The expandable material removal element 16 can be positioned within the pilot hole and the dilating member 158, if provided, can be expanded to provide added stability to the distally-located portions of the device 142 or to occlude blood flow through the vascular lumen. At this point, the expandable material removal element 16 can be expanded, according to the above-discussed processes, within the pilot hole so that the braided wires 102 engage the occlusion material. This method is substantially similar to that illustrated in FIG. 16 with respect to the embodiments 176. The spring-like properties of the wires 102 can allow the removal element 16 to conform to the configuration of the occlusion when expanded, as will be discussed in greater detail later. The motor 24 can again be energized, and the rotating material removal element 16 can remove additional occluding material. The removal elements 16 may be expanded while the motor 24 is running.

In any case, once sufficient occlusion material has been removed, it may be desirable to perform balloon angioplasty within the vascular lumen in order to displace any remnants of the occlusion. To perform both occlusion material removal and angioplastic displacement of an occlusion remnant, the removal device 142 is used. After the motor 24 and the rotation of the expandable material removal element 16 has been stopped, the material removal element 16 is moved into the contracted position so that the braided wires 102 of the removal device 142 define a low profile. If the dilating member 158 was expanded during operation of the material removal element 16, then it too should be deflated, by reversing the above-discussed pressure flow, so that the entire distal portion of the removal device 142 defines a low profile for facilitating intravascular movement of the removal device 142.

The catheter assembly 146 of the removal device 142 is shifted distally within the vascular lumen to locate the contracted dilating member 158 adjacent the remnants of the occlusion. The treating physician may have an easier time of properly positioning the dilating member 158 with respect to the occlusion remnants because the marker band 164 renders the position of the dilating member 158 radioscopically visible. Once proper position has been attained, the dilating member 158 can be inflated, as discussed above, to a sufficient pressure, typically on the order of 4 to 8 atmospheres, to displace the remnants and further revascularize the vascular lumen.

A further method of removing occlusion material begins with locating the removal element 16, in the contracted position, distally of the occlusion material. The removal element 16 is expanded, as described above, and is then shifted proximally in the lumen towards the occlusion. The removal element 16 may be energized such that the rotating removal element 16 removes occlusion material from a distal end of the occlusion upon contact with the occlusion. The removal element 16 can be moved proximally progressively until sufficient occlusion material has been removed to revascularize the lumen.

A variation of this method is illustrated in FIG. 17 with respect to the removal device 218. FIG. 17 shows the removal element 16 located distally of the occlusion 224. This location of the removal element 16 may be achieved if the non-occluded lumen through the occlusion 224 is sufficient to accept the removal element 16 in the contracted position, or by forming a pilot hole through the occlusion 224 as discussed hereinabove. The removal element 16 is moved towards the expanded position by operation of the expansion control mechanism 184 to deploy the wires 102 to remove occlusion material and to deploy the collection portion 220 to capture particulate 222.

Once expanded, the removal element 16 is energized and the element 16 and the removal device 218 are moved proximally against the occlusion 224. The wires 102 remove particulate 222 from a distal portion of the occlusion 224. Because the collection portion 220 is located distally of the abrasive-coated wires 102 and the occlusion 224, particulate 222 removed from the occlusion 224 moves towards the collection portion 220 under the influence of fluid flowing through the vascular lumen. As noted earlier, fluid may be supplied through the catheter shaft 188 to do this, although blood flow through the lumen may be sufficient.

As the particulate 222 is removed from the occlusion 224, the particulate 222 moves into the interior of the removal element 16 through the spaces between adjacent abrasive-coated wires 102 and into the collection chamber 228 defined by the retention member or coating 226. The coating 226 retains the particulate 222 within the collection chamber 228 while allowing fluid to flow therethrough. The energized removal element 16 is progressively moved proximally against the occlusion 224. The location of occlusion material removal, defined by contact between the abrasive-coated wires 102 and the occlusion 224, is always proximal of the location of particulate 222 collection, defined by the coating 226. Some, if not all, of the particulate 222 removed from the occlusion 224 should be collected within the collection portion 220. Thus, the collection portion 220 may reduce the amount of particulate 222 that floats away from the occlusion 224 and the removal device 218. Once sufficient occlusion material is removed, or once the collection portion 220 is filled with particulate 222, the removal element 16 can be moved towards the contracted position and removed from the patient. The coating 226 may insure that particulate 222 is retained within the collection portion 220.

According to another method for removing vascular occlusion material, the removal element 16 can be inserted into a vascular lumen and positioned proximally of an vascular occlusion. The removal element 16 can then be expanded, by use of the above-discussed methods, to a certain diameter, such as the diameter of a non-occluded portion of the lumen, and advanced within the lumen towards the occlusion. The removal element 16 is forced into contact with the occlusion, and the wires 102 forming the expanded element 16 bite into the occlusion material. The removal element 16 is then retracted from the occlusion and readied for another advance towards the occlusion. At any point, the removal element 16 can be collapsed and retracted, as may be desirable to determine the composition of the occlusion material, or may be contracted or further expanded, such as discussed above, to define different cutting diameters. The steps of this method can be repeated as often as desired.

Still a further method takes advantage of a property provided by the removal element 16, viz. the removal element 16 can absorb forces applied to it and correspondingly deform or deflect. This method also takes advantage of the ability of the drive shaft 92 to axially expand or contract during operation. These property may be more readily understood with reference to FIGS. 11 and 16. FIG. 11 illustrates a cross section of a vascular lumen 166 occluded by occluding material 168. The occluding material 168 defines an eccentric surface 170 offset from the vascular lumen 166 by a distance which defines a non-occluded diameter in the vascular lumen 166. The removal element 16 is inserted into the non-occluded diameter and expanded, as discussed above, until an outer surface of the removal element 16 contacts the eccentric surface 170. Because the removal element 16 can absorb forces applied to it, such as those attendant with expansion or rotation of the removal element 16, the removal element 16 deflects or deforms such that the removal element 16 defines a configuration which complements the corresponding configuration of the eccentric surface 170. Thus, the removal element 16 can take into account varying occlusion morphology.

Once the removal element 16 has assumed the complementing configuration, as shown in FIG. 16, the motor 24 is activated and the removal element 16 begins to rotate within the non-occluded diameter. Deflection of the removal element 16 formed by the wires 102 causes longitudinal or axial and radial cutting actions or vectors to be reduced correspondingly. This may reduce the probability that healthy tissues might be removed because a cushioned, softer engagement may be formed between the healthy tissues and the removal element 16 due to the spring-like nature of the removal element 16. In addition, because the configuration of the removal element 16 conforms to the configuration of the occlusion material 168, upon rotation of the element 16, a greater concentration of removing forces can be generated at an area, indicated generally by reference numeral 172, on the occlusion material 168 than the force concentration present at an area 174 on the vascular lumen 166. Specifically, cutting forces may be evenly distributed over the area 174. This can lead to more efficient removal of vascular occlusion material 168.

Furthermore, it is to be noted that the spring-like nature of the removal element 16 provides for another method for removing vascular occlusion material. Specifically, according to this method, the removal element 16 may be placed within a lumen constricted or reduced by an occlusion such that the wires 102 are in proper position with respect to the occlusion for removal of occlusion material 168. At this point, the wire lock mechanism 50 and the removal element expansion control mechanism 52 for the removal devices 10 and 142, or the expansion control mechanism 184 for the removal devices 176 and 218 can be actuated, as described hereinabove, in order to expand the removal element 16 to define a diameter equal to a non-occluded diameter of the same vascular lumen, i.e. the diameter of the vascular lumen with the occlusion material removed.

The removal element 16 expands to define a configuration which corresponds to the configuration of the eccentric surface 170, as shown in FIG. 11 and as similarly depicted in FIG. 16. However, because the occlusion material 168 prevents the removal element 16 from immediately expanding to define the non-occluded diameter, the wires 102 of the element 16 absorb and store expanding forces in the form of spring energy. This stored spring energy allows the removal element 16 to be essentially self-expanding during operation of the removal device 10, 142, 176 or 218.

Specifically, the motor 24 is energized and the removal element 16 begins to rotate within the lumen 166, thereby removing vascular occlusion material 168 from the occlusion. As progressively more and more occlusion material 168 is removed from the occlusion, the spring energy stored within the wires 102 of the element 16 is released which causes the removal element 16 to expand further responsive to the amount of occlusion material 168 removed. Stored spring energy may also be released if the drive shaft 92 axially expands or contracts during operation. The stored spring energy is progressively released as greater amounts of occlusion material 168 are removed until the braided removal element 16 is expanded to the degree indicated by the removal element expansion control mechanism 52 or the expansion control mechanism 184. The removal element expansion limiting means also insures that the removal element 16 is not over-expanded. The removal element 16 ceases to expand once sufficient occlusion material 168 has been removed and once sufficient stored spring energy has been released. At this point, the diameter defined by the expanded removal element 16 should be approximately equal to the original, non-occluded diameter of the vascular lumen 166.

The self-expanding nature of the removal element 16 provides another method of removing vascular occlusion material from a vascular lumen. According to this method, the removal element 16 is pre-formed or expanded such that the element 16 defines a certain, pre-determined configuration. By placing the removal element 16 in this configuration, the element 16 is provided with a memory of this shape. Forming the element 16 with shape memory alloys, such as nitinol and the like, also insures effective shape or configuration memory. The pre-formed configuration preferably has dimensions suitable for intravascular insertion and navigation. The pre-formed removal element 16 is positioned adjacent the occlusion material, which defines a non-occluded diameter within the vascular lumen. The removal element 16 is then inserted into the non-occluded lumen.

Contact of the removal element 16 with the occlusion material imparts forces to the braided wires 102 which deform the configuration of the removal element 16. The spring-like nature of the braided wires 102 comprising the removal element 16 allows the element 16 to deform or otherwise comply to a configuration defined by the occlusion material, as illustrated in FIGS. 11 and 16. The element 16 can now be energized so that occlusion material can be removed. As progressively more occlusion material is removed, the shape memory of the wires 102 allows the element 16 to move towards the initial, pre-determined configuration. Once sufficient occlusion material has been removed, the memory aspects of the removal element 16 allow it to recover from its deformed state to its original configuration.

As is evident from the foregoing discussion, the embodiments of the present invention provide treating physicians with a number of methods for performing intravascular treatments. The individual steps comprising these methods can be performed in any order, and steps of one method can be combined with steps of other methods to achieve desired results. By providing an expandable material removal element 16, the embodiments of the invention provide a plurality of material removal element 16 sizes, shapes and cutting profiles or characteristics combined in a single intravascular occlusion material removal device 10, 142, 176 or 218. These shapes, sizes and characteristics are positively variable by the controlled incremental expansion of the material removal element 16 offered by the guidewire lock mechanism 50 and the material removal element expansion control mechanism 52 or the expansion control mechanism 184. Also, the various constructions of the material removal element radial expansion limiting means prevents over-expansion of the material removal element 16. It is to be noted that more efficient removal of vascular occlusion material may be possible if the motor 24 is energized prior to moving the removal element 16 towards the expanded position because the removal element 16 will gain momentum prior to engagement with the occlusion material.

By combining the material removal element 16 with the cutting surface 108, a plurality of differently directed cutting actions can be performed by the removal devices 10. 142, 176 and 218. Specifically, the material removal element 16 is capable of producing cutting actions directed radially and tangentially with respect to the vascular lumen or occlusion. In addition, the cutting surface 108 can produce cutting actions directed tangentially and longitudinally with respect to the vascular lumen or occlusion. Thus, at least three differently directed cutting actions can be produced by the removal devices 10, 142, 176 and 218. In addition, the occlusion material can be cut, ground, displaced, captured or aspirated. Specifically, relatively soft occlusion material can be sliced or cut by the wires 102 and fall into the hollow interior of the removal element 16, while relatively hard occlusion material can be ground by the abrasive 105 on the wires 102. Occlusion material can be retained within the collection chamber 228 by the coating 226. Thus, a treating physician can have greater flexibility in performing intravascular treatments while using only one device 10, 142, 176 or 218.

While preferred embodiments of the present invention are shown and described, it is envisioned that those skilled in the art may devise various modifications of the embodiments of the present invention without departing from the spirit and scope of the appended claims.

We claim:

1. An intravascular device for removing vascular occlusion material within a vascular lumen in a patient, wherein the occlusion material defines a configuration, the intravascular device comprising:

an expandable material removal element having first and second ends and including a plurality of wires disposed between the first and second ends;

a catheter shaft extending to the first end of the expandable material removal element;

a drive shaft for energizing the material removal element intravascularly; the drive shaft having a proximal end and a distal end, the drive shaft being connected to the second end of the material removal element proximate the distal end of the drive shaft extending through the material removal element and being shiftable with respect to the material removal element and the catheter shaft; the drive shaft being disposed within the catheter shaft; the material removal element being expandable responsive to shifting of the drive shaft; and the expandable removal element being sufficiently deformable so that the element assumes a configuration corresponding to the configuration defined by the non-occluded diameter upon expansion of the element; and a collection portion disposed on the material removal element for collecting removed occlusion material, the collection portion including a retention member disposed on the wires of the removal element.

2. An intravascular device as defined in claim 1 further comprising:

a motor operatively connected to the drive shaft proximate the proximal end of the drive shaft for rotating the expandable material removal element intravascularly; wherein removing force is generated by rotation of the element intravascularly for removing vascular occlusion material; and wherein the configuration of the removal element relatively concentrates removing force on the occlusion material upon rotation of the removal element.

3. An intravascular device as defined in claim 1 further comprising:

means operatively connected to the removal element for rotating the element intravascularly, rotation of the element generating a force which is relatively concentrated on the occlusion material as compared to the vascular lumen.

4. A method for removing occlusion material from a vascular lumen within a patient comprising the steps of:

a) providing an occlusion material removal device having an expandable material removal element, a single rotatable drive shaft and a catheter shaft, the removal element having first and second ends, the catheter shaft extending to the first end and the drive shaft being connected to the second end, the single rotatable drive shaft extending through the material removal element, and the material removal element being variably expandable responsive to shifting of the single rotatable drive shaft with respect to the removal element and the catheter shaft;

b) navigating the material removal element distally through the occlusion material;

c) shifting the single rotatable drive shaft with respect to the material removal element and the catheter shaft thereby expanding the removal element; and d) moving the expanded material removal element proximally within the vascular lumen to engage the occlusion material.

5. A method as defined in claim 4 further comprising the step of:

e) positioning the material removal element in a contracted position distally of the occlusion material.

6. A method as defined in claim 4 wherein the providing step a) includes providing a collection portion on a distal portion of the material removal element for collecting removed occlusion material, and further comprising the step of:

e) collecting removed occlusion material in the collection portion.

7. A method as defined in claim 6 wherein the shifting step c) comprises shifting the single rotatable drive shaft with respect to the removal element to deploy the collection portion.

8. A vascular occlusion material removal device for removing vascular occlusion material in a vascular lumen, the removal device comprising:

an expandable material removal element having a distal end and a proximal end insertable intravascularly into a patient;

a catheter shaft extending to the proximal end of the removal element;

a drive shaft disposed through the removal element and connected to the distal end of the expandable material removal element; the drive shaft being shiftable within the material removal element; the material removal element being expandable responsive to shifting of the drive shaft with respect to the removal element and the catheter shaft; the drive shaft being disposed within the catheter shaft;

a plurality of braided wires comprising the removal element; and an abrasive disposed on the wires for removing vascular occlusion material.

9. A vascular occlusion material removal device as defined in claim 8 further comprising: a retention member disposed on the removal element for collecting removed occlusion material.

10. A vascular occlusion material removal device as defined in claim 9 wherein the retention member comprises a filter.

11. A vascular occlusion material removal device as defined in claim 9 wherein the retention member comprises a fabric.

12. A vascular occlusion material removal device as defined in claim 9 wherein the retention member comprises a polymeric coating.

13. A vascular occlusion material removal device as defined in claim 9 wherein the abrasive and the retention member are located on opposite ends of the removal element.

14. A vascular occlusion material removal device as defined in claim 9 wherein the retention member includes an aperture for permitting fluid flow therethrough.

15. A vascular occlusion material removal device as defined in claim 14 wherein the aperture has a diameter measuring about 5 microns.

16. A vascular occlusion material removal device for removing vascular occlusion material in a vascular lumen, the removal device comprising:

an expandable material removal element insertable intravascularly into a patient, the removal element having first and second ends;

a catheter shaft extending to the first end;

a drive shaft disposed through and connected to the second end of the expandable material removal element for energizing the removal element; the drive shaft being disposed within the catheter shaft; the drive shaft being shiftable with respect to the material removal element and the catheter shaft; the material removal element being expandable responsive to shifting of the drive shaft;

a plurality of braided wires comprising the removal element; and the wires being made from a super-elastic alloy.

17. A vascular occlusion material removal device as defined in claim 16 wherein the super-elastic alloy is nitinol.

18. A method for removing vascular occlusion material from a vascular lumen comprising the steps of:

providing a vascular occlusion material removal device having an expandable occlusion material removal element, the removal element having first and second ends, the removal element including a plurality of braided wires and an abrasive disposed on the wires;

providing a catheter shaft extending to the first end of the removal element;

providing a drive shaft disposed in and connected to the second end of the removal element, the drive shaft being shiftable with respect to the removal element and the catheter shaft;

intravascularly positioning the removal element distally of the occlusion material;

shifting the drive shaft with respect to the removal element and the catheter shaft to expand the element intravascularly; and moving the removal element proximally within the vascular lumen to remove occlusion material.

19. A method according to claim 18 further comprising the step of rotating the drive shaft to cause rotation of the removal element intravascularly.

20. A vascular occlusion material removal device for removing vascular occlusion material in a vascular lumen, the material removal device comprising:

an expandable material removal element movable between an expanded position and a contracted position having a distal end and a free-wheeling proximal end;

a catheter shaft having a proximal and a distal end extending to the free-wheeling proximal end of the removal element;

a drive shaft operatively connected to the distal end of the expandable material removal element to rotate the removal element, the drive shaft being shiftable with respect to the removal element and the catheter shaft to move the removal element between the expanded position and the contracted position, the distal end of the catheter shaft surrounding a portion of the drive shaft; and a bearing surface located at the distal end of the catheter variably engageable with the free-wheeling proximal end of the removal element to move the removal element between the expanded position and the contracted position.

21. A vascular occlusion material removal device as defined in claim 20 further comprising a removal element expansion control mechanism for positively controlling movement of the removal element between the expanded position and the contracted position, the control mechanism being at an end of the drive shaft opposite the removal element.

22. A vascular occlusion material removal device as defined in claim 21 wherein the removal element expansion control mechanism includes a groove and a tab; the tab being selectively movable into and out of the groove; and the drive shaft being movable with respect to the removal element responsive to movement of the tab into and out of the groove.

23. A vascular occlusion material removal device as defined in claim 21 wherein the removal element expansion control mechanism includes an actuation portion for accepting force from a treating physician to positively control movement of the removal element between the expanded position and the contracted position.

24. A vascular occlusion material removal device as defined in claim 21 further comprising scaling means operatively associated with the removal element expansion control mechanism for providing an indication of position of the removal element between the expanded position and the contracted position.

25. A vascular occlusion material removal device as defined in claim 20 further comprising
   c) a catheter having a distal end surrounding a portion of the drive shaft;
   d) a bearing surface located at the distal end of the catheter variably engagable with the free-wheeling proximal end of the removal element to move the removal element between the expanded position and the contracted position.

26. A vascular occlusion material removal device as defined in claim 20 further comprising a bearing surface located at the free-wheeling proximal end of the removal element; and wherein the bearing surface on the free-wheeling proximal end has a configuration for facilitating rotation of the removal element with respect to the catheter.

27. A vascular occlusion material removal device as defined in claim 26 wherein one of the bearing surfaces has an enlarged portion such that the other of the bearing surfaces is rotatable within and relative to the enlarged portion.

28. A vascular occlusion material removal device as deemed in claim 26 wherein one of the bearing surfaces comprises a hypotube.

29. A vascular occlusion material removal device as defined in claim 26 further comprising a lubricous or low friction substance disposed on at least on of the bearing surfaces for facilitating relative rotation of the bearing surfaces.

30. A vascular occlusion material removal device as defined in claim 20 further comprising a collection portion located on the removal element for collecting removed occlusion material.

31. A vascular occlusion material removal device as defined in claim 30 wherein the collection portion comprises a retention member disposed on the removal element.

32. A vascular occlusion material removal device as defined in claim 31 wherein the retention member comprises a fabric filter.

33. A vascular occlusion material removal device as defined in claim 31 wherein the retention member comprises a polymer coated on the removal element.

34. A vascular occlusion material removal device as defined in claim 31 wherein the retention member includes an aperture for allowing fluid to flow therethrough.

35. A vascular occlusion material removal device as defined in claim 34 wherein the aperture has a diameter measuring about 5 microns.

36. A vascular occlusion material removal device as defined in claim 20 further comprising a dilatation member connected to the catheter shaft adjacent the removal element.

37. A method for removing vascular occlusion material from a vascular lumen comprising the steps of:
   a) providing a vascular occlusion material removal device having an expandable occlusion material removal element, the material removal element having first and second ends; a catheter shaft extending to the first end of the removal element; a drive shaft disposed in and connected to the second end of the material removal element; the material removal element being expandable responsive to shifting of the drive shaft with respect to the removal element and the catheter shaft; the catheter shaft surrounding a portion of the drive shaft;
   b) intravascularly navigating the removal element to the occlusion material;
   c) energizing the removal element to remove occlusion material;
   d) supplying a first pressure through the drive shaft;
   e) supplying a second pressure through the catheter; and
   f) generating a pressure differential with the first pressure and the second pressure within the vascular lumen sufficient to draw removed occlusion material into the catheter.

38. A method as defined in claim 37 wherein the providing step a) further comprises providing a dilation member on the material removal device.

39. A method as defined in claim 37 further comprising the step of
   g) inflating the dilation member.

40. A method for removing vascular occlusion material from a vascular lumen comprising the steps of:
   a) providing a vascular occlusion material removal device having an expandable occlusion material removal element, the material removal element having first and second ends; a catheter shaft extending to the first end of the removal element; and a drive shaft operably connected to the second end of the removal element wherein the removal element includes a plurality of braided wires, including an abrasive disposed on the wires;
   b) intravascularly navigating the removal element to the occlusion material;
   c) energizing the removal element to remove occlusion material;
   d) supplying a first pressure through the drive shaft;
   e) supplying a second pressure through the catheter shaft; and
   f) generating a pressure differential with the first pressure and the second pressure within the vascular lumen sufficient to draw removed occlusion material into the catheter.

41. A method as defined in claim 40 wherein the providing step a) further comprises providing a dilation member on the material removal device.

42. A method as defined in claim 41 further comprising the step of g) inflating the dilation member.

43. A vascular occlusion material removal device for removing vascular occlusion material in a vascular lumen, the material removal device comprising:

a) an expandable material removal element having a first and a second end and including a plurality of braid wires generally disposed between the first and second ends of the removal element, and the expandable material removal element being movable between an expanded position and a contracted position;

b) a drive shaft connected to the first end of the expandable material removal element for rotating the removal element;

c) a catheter surrounding a portion of the drive shaft; the catheter having a distal end for operatively variably contracting the second end of the material removal element such that the removal element is rotatable with respect to the catheter; and the catheter being shiftable with respect to the drive shaft for moving the material removal element between the expanded position and the contracted position.

44. A vascular occlusion material removal device as defined in claim 43 further comprising d) a prime mover operatively connected to the drive shaft for rotating the drive shaft with respect to the catheter.

45. A vascular occlusion material removal device as defined in claim 44 wherein the prime mover rotates the material removal element intravascularly at a rate of about 20,000 revolutions per minute.

46. A vascular occlusion material removal device as defined in claim 44 wherein the prime mover rotates the material removal element intravascularly at a rate substantially within the range of 0 to 100,000 revolutions per minute.

47. A vascular occlusion material removal device as defined in claim 44 wherein the prime mover comprises a direct current electric motor.

48. A vascular occlusion material removal device as defined in claim 43 further comprising at least eight braided wires.

49. A vascular occlusion material removal device as defined in claim 43 wherein the wires are made of a super-elastic alloy.

50. A vascular occlusion material removal device as defined in claim 43 further comprising an abrasive disposed on the wires.

51. A vascular occlusion material removal device as defined in claim 50 wherein the abrasive comprises at least one of a diamond grit and a synthetic abrasive disposed onto the wires.

52. A vascular occlusion material removal device as defined in claim 43 further comprising d) a cutting surface disposed distally of the removal element for removing vascular occlusion material, the cutting surface being connected to the removal element at the first end of the removal element.

53. A vascular occlusion material removal device as defined in claim 43 wherein the expandable material removal element has an axial length and a radius; and wherein the axial length is reducible responsive to shifting of the catheter, thereby expanding the radius.

54. A vascular occlusion material removal device as defined in claim 43 wherein the expandable removal element comprises a plurality of wires; and wherein the wires are braided thereby enabling the wires to store spring energy during expansion of the removal element.

55. A vascular occlusion removal device as defined in claim 43 further comprising means for limiting expansion of the expandable material removal element.

56. A vascular occlusion material removal device as defined in claim 43 wherein the drive shaft comprises a coil having a proximal end and a distal end; wherein a braid having a proximal end and a distal end surrounds at least a portion of the coil; wherein the proximal end of the braid is attached to the proximal end of the coil; wherein the distal end of the braid is attached to the coil at a location offset proximally of the distal end of the coil; and wherein the braid is tensioned between the proximal end and distal end thereof.

57. A vascular occlusion material removal device as defined in claim 43 wherein the drive shaft comprises a coil having a proximal end and a distal end; wherein a braid having a proximal end and a distal end surrounds the coil; wherein the proximal end of the braid is attached to the proximal end of the coil; wherein the distal end of the braid is attached to the distal end of the coil; and wherein the braid is tensioned between the proximal end and distal end thereof.

58. A vascular occlusion material removal device as defined in claim 43 wherein the drive shaft comprises a cylindrical portion having a hollow interior and a coiled portion; and further comprising an aperture in the cylindrical portion for allowing fluid to flow into the hollow interior of the cylindrical portion.

59. A vascular occlusion material removal device as defined in claim 58 further comprising a manifold assembly; further comprising a lumen within the manifold assembly for accepting the cylindrical portion; and further comprising a fluid seal within the lumen for insuring that fluid within the lumen flows through the aperture into the hollow interior.

60. A vascular occlusion material removal device as defined in claim 58 wherein the cylindrical portion has a proximal end; further comprising a fluid seal located at the proximal end of the cylindrical portion for limiting fluid flow proximally of the proximal end of the cylindrical portion.

61. A vascular occlusion removal device as defined in claim 43 further comprising:

d) a removal element movement control mechanism for positively controlling movement of the removal element between the expanded position and the contracted position, the control mechanism being located at an end of the drive shaft opposite the removal element.

62. A vascular occlusion material removal device as defined in claim 61 wherein the removal element movement control mechanism comprises an actuation portion engagable by a physician; the actuation portion being operatively connected to the catheter for transferring force applied to the actuation portion to the catheter; and a tab operatively connected to the actuation portion for allowing positive incremental shifting of the catheter.

63. A vascular occlusion material removal device as defined in claim 43 further comprising a balloon dilating member connected to the catheter for performing at least one of centering the device intravascularly, stabilizing the device intravascularly, occluding fluid flow through a vascular lumen, and angioplasticly displacing occlusion material.

* * * * *